United States Patent
Boustany et al.

(10) Patent No.: US 8,227,419 B2
(45) Date of Patent: Jul. 24, 2012

(54) METHOD OF TREATING CONDITIONS ASSOCIATED WITH AIRWAY TISSUE REMODELING

(75) Inventors: Sarah Boustany, Chipping Norton (AU); Janette Kay Burgess, Wilberforce (AU); Judith Lee Black, Woollahra (AU); Brian Gregory George Oliver, Homebush West (AU)

(73) Assignee: CRC For Asthma and Airways Ltd., Camperdown, NSW (AU)

( * ) Notice: Subject to any disclaimer, the term of this patent is extended or adjusted under 35 U.S.C. 154(b) by 625 days.

(21) Appl. No.: 12/278,266

(22) PCT Filed: Feb. 2, 2007

(86) PCT No.: PCT/AU2007/000106
§ 371 (c)(1),
(2), (4) Date: Jan. 8, 2009

(87) PCT Pub. No.: WO2007/087689
PCT Pub. Date: Aug. 9, 2007

(65) Prior Publication Data
US 2009/0221494 A1 Sep. 3, 2009

Related U.S. Application Data

(60) Provisional application No. 60/764,833, filed on Feb. 3, 2006.

(51) Int. Cl.
*A61K 38/16* (2006.01)
*A61K 38/17* (2006.01)
*A61K 38/10* (2006.01)

(52) U.S. Cl. ............ 514/21.2; 514/21.3; 514/21.4; 514/13.3; 530/300

(58) Field of Classification Search ............ None
See application file for complete search history.

(56) References Cited

U.S. PATENT DOCUMENTS
2006/0172941 A1  8/2006  Rastelli et al.

FOREIGN PATENT DOCUMENTS
| WO | WO 00/59532 | 10/2000 |
| WO | WO 01/51523 A2 | 7/2001 |
| WO | WO 03/059257 A2 | 7/2003 |
| WO | WO 2005/103281 A2 | 11/2005 |
| WO | WO 2006/128027 A1 | 11/2006 |
| WO | WO 2007/033215 A2 | 3/2007 |

OTHER PUBLICATIONS

Wells, J.A. (1990). Additivity of mutational effects in proteins. Biochemistry. 29(37):8509-8517.*
Ngo et al. (1994). Computational complexity, protein structure prediction, and the Levinthal paradox. In Merz and Le Grand (Eds.) The Protein Folding Problem and Tertiary Structure Prediction. Birkhauser:Boston, pp. 491-495.*
Caudroy, S. et al. 2004 "Implication of tumstatin in tumor progression of human bronchopulmonary carcinomas" *Human Pathology*, vol. 35(10): 1218-1222.
Hamano, Y. et al. 2003 "Physiological levels of tumstatin, a fragment of collagen IV alpha 3 chain, are generated by MMP-9 proteolysis and suppress angiogenesis via αVβ3 integrin" *Cancer Cell* 3(6):589-601.
Finlay, G. 2003 "The LAM cell: what is it, where does it come from, and why does it grow?" *Am J Physiol Lung Cell Mol Physiol* 286: L690-L693.
Hamano, Y. et al. 2005 "Tumstatin, the NC1 domain of α3 chain of type IV collagen, is an endogenous inhibitor of pathological angiogensis and suppresses tumor growth" *Biochemical and Biophysical Research Communcations* 333:292-298.
Leath, T.M. et al. 2005 "Novel and emerging therapies for asthma" *Drug Discovery Today* 10(23-24):1647-1655.
Petitclerc, E. et al. 2000 "New Functions for Non-collagenous Domains of Human Collagen Type IV" *The Journal of Biological Chemistry* 275(11):8051-8061.
Rüegg, C. et al. 2006 Antiangiogenic peptides and proteins: From experimental tools to clinical drugs: *Biochimica et Biophysica Act* 1765:155-177.
Serini, G. et al. 2006 "Integrins and angiogenesis: A sticky business" *Experimental Cell Research* 312:651-658.
Supplementary European Search Report dated Aug. 28, 2009 for European Application No. EP07710533.
Maeshima, Y. et al. 2000 "Two RGD-independent $\alpha_v\beta_3$ integrin binding sites on tumstatin regulate distinct anti-tumor properties" *J Biol Chem* 275: 23745-23750.
Maeshima, Y. et al. 2001 "Extracellular matrix-derived peptide binds to $\alpha_v\beta_3$ integrin and inhibits angiogenesis" *J Biol Chem* 276: 31959-31968.

* cited by examiner

*Primary Examiner* — Christine J Saoud
*Assistant Examiner* — Jon M Lockard
(74) *Attorney, Agent, or Firm* — Knobbe Martens Olson & Bear LLP

(57) ABSTRACT

The invention provides a method for improving airway conductance in a subject in need thereof, the method comprising administering to the subject an effective amount of one or more of tumstatin; a derivative, variant or homologue thereof, a polynucleotide encoding tumstatin or a derivative, variant or homologue thereof; or an agent capable of increasing the expression or production of tumstatin.

13 Claims, 18 Drawing Sheets

|  | α1 | α2 | α3 | α4 | α5 | α6 | n |
|---|---|---|---|---|---|---|---|
| Asthmatic | 2 | 3 | 0 | 2 | 2 | 2 | 8 |
| Non-asthmatic | 2 | 2 | 2 | 3 | 2 | 3 | 7 |

0= Absence of stain
1= Discontinuous and thin staining
2= Thin and continuous detection
3= Strong and continuous staining

| | α1 | α2 | α3 | α4 | α5 | α6 | n |
|---|---|---|---|---|---|---|---|
| LAM | 2.2 | 2.3 | 0.5 | 3 | 0.6 | 2 | 10 |

0 = Absence of stain
1 = Discontinuous and thin staining
2 = Thin and continuous detection
3 = Strong and continuous staining

A)	B)

a)

b)

SEQUENCE LISTING

<160> NUMBER OF SEQ ID NOS: 8

<210> SEQ ID NO 1
<211> LENGTH: 20
<212> TYPE: DNA
<213> ORGANISM: Artificial Sequence
<220> FEATURE:
<223> OTHER INFORMATION: Oligonucleotide

```
<400> SEQUENCE: 1
gttgcacgtt cctcttccat                                               20

<210> SEQ ID NO 2
<211> LENGTH: 20
<212> TYPE: DNA
<213> ORGANISM: Artificial Sequence
<220> FEATURE:
<223> OTHER INFORMATION: Oligonucleotide

<400> SEQUENCE: 2
agccaaacca ctgacattcc                                               20

<210> SEQ ID NO 3
<211> LENGTH: 20
<212> TYPE: DNA
<213> ORGANISM: Artificial Sequence
<220> FEATURE:
<223> OTHER INFORMATION: Oligonucleotide

<400> SEQUENCE: 3
tcacggctgg atttctctct                                               20

<210> SEQ ID NO 4
<211> LENGTH: 20
<212> TYPE: DNA
<213> ORGANISM: Artificial Sequence
<220> FEATURE:
<223> OTHER INFORMATION: Oligonucleotide

<400> SEQUENCE: 4
tcacggctgg atttctctct                                               20

<210> SEQ ID NO 5
<211> LENGTH: 20
<212> TYPE: DNA
<213> ORGANISM: Artificial Sequence
<220> FEATURE:
<223> OTHER INFORMATION: Oligonucleotide

<400> SEQUENCE: 5
ggaattcttc caggcaggag                                               20

<210> SEQ ID NO 6
<211> LENGTH: 20
<212> TYPE: PRT
<213> ORGANISM: Homo sapiens

<400> SEQUENCE: 6

Leu Gln Arg Phe Thr Thr Met Pro Phe Leu Phe Cys Asn Val Asn Asp
 1               5                  10                  15

Val Cys Asn Phe
            20

<210> SEQ ID NO 7
<211> LENGTH: 25
<212> TYPE: PRT
<213> ORGANISM: Homo sapiens

<400> SEQUENCE: 7

Thr Met Pro Phe Leu Phe Cys Asn Val Asn Asp Val Cys Asn Phe Ala
 1               5                  10                  15

Ser Arg Asn Asp Thr Ser Thr Trp Leu
            20                  25
```

```
<210> SEQ ID NO 8
<211> LENGTH: 15
<212> TYPE: PRT
<213> ORGANISM: Homo sapiens

<400> SEQUENCE: 8

Thr Met Pro Phe Leu Phe Cys Asn Val Asn Asp Val Cys Asn Phe
1               5                   10                  15
```

METHOD OF TREATING CONDITIONS ASSOCIATED WITH AIRWAY TISSUE REMODELING

This application is U.S. National Phase of International Application PCT/AU2007/000106, filed Feb. 2, 2007 designating the U.S., and published in English as WO 2007/087689 on Aug. 9, 2007, which claims priority to U.S. Provisional Application No. 60/764,833, filed Feb. 3, 2006.

REFERENCE TO SEQUENCE LISTING

The present application is filed along with a Sequence Listing in electronic format. The Sequence Listing is provided as a file entitled 12903741_1.txt, created Mar. 9, 2012, which is approximately 2.01 Kb in size. The information in the electronic format of the Sequence Listing is incorporated herein by reference in its entirety.

FIELD OF THE INVENTION

The present invention relates to methods of modulating tissue remodelling and airway conductance and to agents useful for same. More particularly, the present invention relates to a method of modulating airway tissue remodelling and agents useful for same. Methods of the present invention are useful, inter alia, in relation to the treatment and/or prophylaxis of conditions characterised by unwanted tissue remodelling, in particular unwanted airway tissue remodelling, such as asthma and lymphangioleiomyomatosis (LAM). The present invention further provides a means of diagnosing the occurrence or predisposition to the occurrence of unwanted airway tissue remodelling.

BACKGROUND OF THE INVENTION

Bibliographic details of the publications referred to by author in this specification are collected alphabetically at the end of the description.

The disclosure of every patent, patent application, and publication cited herein is hereby incorporated herein by reference in its entirety.

The citation of any reference herein should not be construed as an admission that such reference is available as "Prior Art" to the present application. Further, the reference in this specification to any prior publication (or information derived from it), or to any matter which is known, is not, and should not be taken as an acknowledgment or admission or any form of suggestion that that prior publication (or information derived from it) or known matter forms part of the common general knowledge in the field of endeavour to which this specification relates.

Asthma is a chronic, episodic disease of the airways. In 1997, the National Heart, Lung, and Blood Institute in the United States included the following features as integral to the definition of asthma;
(i) recurrent episodes of respiratory symptoms;
(ii) variable airflow obstruction that is often reversible, either spontaneously or with treatment;
(iii) presence of airway hyperresponsiveness and
(iv) chronic airway inflammation in which many cells and cellular elements play a role, in particular, mast cells, eosinophils, T lymphocytes, macrophages, neutrophils, and epithelial cells.

All of these features need not be present in any given asthmatic patient. Although the absolute "minimum criteria" to establish a diagnosis of asthma is not widely agreed upon, the presence of airway hyperresponsiveness is a common finding in patients with current symptoms and active asthma.

Clinicians have long known that asthma is not a single disease. Rather, it exists in several forms. This heterogeneity has been established by a variety of studies which have indicated disease risk from early environmental factors and susceptibility genes; and subsequent disease induction and progression from inflammation as well as response to therapeutic agents. Asthma is an inflammatory disease and is not simply due to excessive smooth muscle contraction. Asthma is a chronic disease of the airways, however it is unknown whether inflammation initiates asthma or whether asthma initiates inflammation. In the lungs of healthy individuals inflammation is a common occurrence, and is in fact necessary to maintain normal lung homeostasis through the removal of pathogens such as bacteria and viruses and pollutants which are present in the air. In the lungs of an asthmatic, an exaggerated response occurs in response to irritants which results in an increased tendency to produce excessive airway narrowing (hyperresponsiveness). Increased airway inflammation follows exposure to inducers such as allergens, viruses, exercise, or non-specific irritant inhalation. Increased inflammation leads to exacerbations characterized by dyspnea, wheezing, cough, and chest tightness. Abnormal histopathologic lesions including oedema, epithelial cell desquamation, and inflammatory cell infiltration are found not only in severe asthma cases but even in patients with very mild asthma.

Asthma is therefore a disease in which inflammation of the airways causes airflow obstruction. When an asthma attack occurs, the muscles of the bronchial tree become tight and the lining of the air passages swells, reducing airflow and producing the characteristic wheezing sound. Mucus production is increased. Most people with asthma exhibit periodic wheezing attacks separated by symptom-free periods. Some asthmatics exhibit chronic shortness of breath with episodes of increased shortness of breath. Other asthmatics may exhibit coughing as their predominant symptom. Asthma attacks can last minutes to days, and can become dangerous if the airflow becomes severely restricted.

In sensitive individuals, asthma symptoms can be triggered by inhaled allergens (allergy triggers), such as pet dander, dust mites, cockroach allergens, molds, or pollens. Asthma symptoms can also be triggered by respiratory infections, exercise, cold air, tobacco smoke and other pollutants, stress, food, or drug allergies. Aspirin and other non-steroidal anti-inflammatory medications provoke asthma in some patients.

Asthma is the Western world's most widespread chronic health problem. In Australia alone, it affects over 2 million Australians:
1 in 4 children
1 in 7 teenagers
1 in 10 adults.

Asthma treatment is aimed at avoiding known allergens and respiratory irritants and controlling symptoms and airway inflammation through medication. In terms of medication, there are two basic classes of medication for the treatment of asthma:
(i) Long term control medications—used on a regular basis to prevent attacks, not for treatment during an attack:
  inhaled steroids (e.g. triamcinolone acetonide, beclomethasone, flunisolide, fluticasone propionate, and budesonide) prevent inflammation
  leukotriene inhibitors (e.g. montelukast sodium, zafirlukast)
  long-acting bronchodilators (e.g. formoterol, salmeterol) help keep airways open cromolyn sodium or nedocromil sodium
theophylline
combination of corticosteroid and bronchodilator, using either separate inhalers or a single inhaler (e.g. fluticasone/salmeterol and budesonide/formoterol).
anti-IgE therapy (e.g. omalizumab).
(ii) Quick relief (rescue) medications—used to relieve symptoms during an attack:
short-acting bronchodilators (e.g. salbutamol, fenoterol, terbutaline, and albuterol) aminophylline
(iii) In addition, oral or intravenous corticosteroids (e.g. prednisone, methylprednisolone) are used to stabilize severe episodes.

Nevertheless, despite significant progress in terms of understanding the cellular basis of asthma and the development of a range of treatment options, the cause of asthma is not known, nor has there been a cure developed. Accordingly, there is an ongoing need to pursue asthma-related research at the level of both understanding its cause and developing new treatment regimens which can contribute to expanding the existing range of therapeutic and prophylactic treatments which are available to the public.

To this end, one aspect of asthma etiology which remains relatively poorly understood is the occurrence of airway tissue remodelling. The natural history of airway remodelling is poorly understood and although it occurs in many patients with asthma, it is not always a universal finding. Pathologically, airway remodelling appears to have a variety of features that include an increase in smooth muscle mass, mucus gland hyperplasia, persistence of chronic inflammatory cellular infiltrates, release of fibrogenic growth factors along with collagen deposition. Many biopsy studies show these pathological features from the airways of patients with chronic asthma. However, there are many unanswered questions, including whether features of remodelling are related to an inexorable progression of acute or chronic airway inflammation or whether remodelling is a phenomenon separate from inflammation altogether.

Lymphangioleiomyomatosis (LAM) is a rare lung disease that affects only females, usually in their thirties, and for which the prognosis is generally extremely poor. Until recently, it was thought that survival rates post-diagnosis were about 10 yrs, but this has been revised and current estimates are closer to 15 yrs. Although the pathogenesis remains unclear, an association with tuberous sclerosis (TSC) is largely accepted (39% of TSC patients have LAM); however, this is not universal. The LAM cell is thought to be a form of smooth muscle that is abnormally proliferative and underlies the formation of characteristic LAM nodules in the lung and angiolipomas in the kidney. The pulmonary nodules are responsible for cystic destruction of the lung, recurrent pneumothoraces and a steady decline in pulmonary function. There is some debate as to whether the abnormal smooth muscle cell arises in the airway or the vasculature and some have suggested that it may be a result of a distant metastasis. The LAM smooth muscle cell is heterogeneous and LAM cells may differ in their degree of differentiation. Ultimately the hyperproliferation of LAM cells in the lungs of affected individuals leads to a reduction in the transfer of oxygen and will result in respiratory failure. Current treatment options have been ineffective in reversing disease progression, and for many affected individuals lung transplantation is used as the last resort.

Accordingly, there remains a need for effective therapeutic and prophylactic options for the treatment of diseases and conditions associated with airway tissue remodelling, such as asthma and LAM.

SUMMARY OF THE INVENTION

The present invention is predicated on the inventors' surprising finding that the expression levels of an endogenously expressed airway tissue molecule, tumstatin (the non-collagenous (NC1) domain of the α3 chain of collagen type IV), are significantly downregulated in airway tissues which have undergone remodelling. By upregulating the levels of this molecule in the airway tissue, for example normalising endogenous levels, the occurrence of tissue remodelling can be reduced. Similarly, as described herein, upregulation of tumstatin also results in an increase in airway conductance. These findings have therefore enabled the development of a method of reducing the incidence and/or severity of tissue remodelling in patients exhibiting airway diseases such as asthma or LAM. In the context of asthma, although not of itself a cure, this finding is extremely valuable in that it provides an adjunctive treatment regimen directed to minimising the occurrence of this form of tissue "scarring". Accordingly, there is provided a means of reducing the severity of one of the more serious consequences of both managed and unmanaged forms of airway diseases such as asthma.

According to a first aspect the present invention provides a method for improving airway conductance in a subject in need thereof, the method comprising administering to the subject an effective amount of one or more of tumstatin; a derivative, variant or homologue thereof; a polynucleotide encoding tumstatin or a derivative, valiant or homologue thereof, or an agent capable of increasing the expression or production of tumstatin.

The subject may suffer from or is predisposed to a condition associated with airway tissue remodelling. The condition may be selected from, for example, asthma, lymphangioleiomyomatosis (LAM), pulmonary fibrosis and cystic fibrosis.

According to a second aspect the present invention provides a method for the treatment and/or prophylaxis of a condition characterised by aberrant or otherwise unwanted airway tissue remodelling in a subject, said method comprising normalising tumstatin levels in said tissue relative to normal endogenous levels wherein normalising said tumstatin level downregulates said airway tissue remodelling.

The condition may be selected from, for example, asthma, LAM, pulmonary fibrosis and cystic fibrosis. The airway tissue may be tracheal, bronchus or bronchiolar tissue.

Typically the method comprises administering to the subject an effective amount of one or more of tumstatin; a derivative, variant or homologue thereof; a polynucleotide encoding tumstatin or a derivative, variant or homologue thereof; or an agent capable of increasing the expression or production of tumstatin.

According to a third aspect the present invention provides a method for the treatment and/or prophylaxis of LAM in a subject, said method comprising normalising the levels of collagen IV α5 chain NC1 domain in the tracheal, bronchus and/or bronchiolar tissue of the subject relative to normal endogenous levels. The method may further comprise normalising the levels of tumstatin in the tracheal, bronchus and/or bronchiolar tissue of the subject relative to normal endogenous levels.

According to a fourth aspect the present invention provides a method of regulating the occurrence of airway tissue remodelling in a subject, said method comprising modulating the level of tumstatin in airway tissue of the subject, wherein normalising tumstatin levels in said tissue relative to normal endogenous levels downregulates the occurrence of tissue remodelling and decreasing tumstatin levels in said tissue relative to normal endogenous levels facilitates the occurrence of tissue remodelling.

Wherein said remodelling is downregulated, the method typically comprises normalising tumstatin levels relative to normal endogenous levels. Levels of tumstatin may be normalised by administering an effective amount of one or more of tumstatin; a derivative, variant or homologue thereof; a polynucleotide encoding tumstatin or a derivative, variant or homologue thereof; or an agent capable of increasing the expression or production of tumstatin.

In an embodiment the derivative is a tumstatin-derived peptide. The tumstatin-derived peptide may comprise the amino acid sequence set forth in SEQ ID NO: 6 or SEQ ID NO:7.

Wherein said remodelling is upregulated, the method typically comprises decreasing tumstatin levels relative to normal endogenous levels. Tumstatin levels may be decreased by administering an effective amount of an antagonist of tumstatin or an agent capable of decreasing the expression or production of tumstatin.

According to a fifth aspect the present invention provides a method for diagnosing a condition associated with aberrant or otherwise unwanted airway tissue remodelling, or susceptibility thereto, in a subject, the method comprising determining the level of tumstatin in airway tissue or cells of the subject.

According to a sixth aspect the present invention provides a method for diagnosing LAM, or susceptibility thereto, in a subject, the method comprising determining the level of collagen IV α5 chain NC1 domain in airway tissue or cells of the subject. The method may further comprise determining the level of tumstatin in airway tissue or cells According to a seventh aspect the present invention provides the use of an agent capable of increasing the level of tumstatin in the airway tissue of a subject in the manufacture of a medicament for the regulation of airway conductance in the subject, wherein normalising tumstatin levels in said tissue relative to normal endogenous levels improves airway conductance.

The agent may be selected from tumstatin; a derivative, variant or homologue thereof; a polynucleotide encoding tumstatin or a derivative, variant or homologue thereof; or an agent capable of increasing the expression or production of tumstatin.

According to an eighth aspect the present invention provides the use of an agent capable of modulating the level of tumstatin in the airway tissue of a subject in the manufacture of a medicament for the regulation of airway tissue remodelling in said subject, wherein normalising tumstatin levels in said tissue relative to normal endogenous levels downregulates the occurrence of tissue remodelling and decreasing tumstatin levels in said tissue relative to normal endogenous levels facilitates the occurrence of tissue remodelling.

According to a ninth aspect the present invention provides the use of an agent capable of modulating the level of tumstatin in the airway tissue of a subject in the manufacture of a medicament for the treatment of a condition characterised by aberrant or otherwise unwanted airway tissue remodelling, wherein normalising tumstatin levels in said tissue relative to normal endogenous levels downregulates the occurrence of tissue remodelling and decreasing tumstatin levels in said tissue relative to normal endogenous levels facilitates the occurrence of tissue remodelling.

According to a tenth aspect the present invention provides a pharmaceutical composition when used for improving airway conductance, downregulating airway tissue remodelling, or treating or preventing a condition associated with reduced airway conductance and/or aberrant airway remodelling, the composition comprising one or more of tumstatin; a derivative, variant or homologue thereof; a polynucleotide encoding tumstatin or a derivative, variant or homologue thereof; or an agent capable of increasing the expression or production of tumstatin, optionally together with. and one or more pharmaceutically acceptable carriers and/or diluents According to an eleventh aspect the present invention provides a diagnostic kit for assaying biological samples comprising an agent for detecting tumstatin or encoding nucleic acid molecules and reagents suitable for facilitating the detection by the agent.

A further aspect of the present invention is directed to a method for the treatment and/or prophylaxis of a condition characterised by aberrant or otherwise unwanted airway tissue remodelling in a mammal, said method comprising modulating the level of tumstatin in the airway tissue of said mammal wherein normalising tumstatin levels in said tissue relative to normal endogenous levels downregulates the occurrence of tissue remodelling and decreasing tumstatin levels in said tissue relative to normal endogenous levels facilitates the occurrence of tissue remodelling.

Still another further aspect of the present invention provides a method for the treatment and/or prophylaxis of asthma in a mammal, said method comprising normalising tumstatin levels in the tracheal, bronchus and/or bronchiolar tissue of said mammal relative to normal endogenous levels wherein normalising said tumstatin level downregulates tissue remodelling in said tracheal, bronchus and/or bronchiolar tissue.

Yet another further aspect of the present invention provides a method for the treatment and/or prophylaxis of LAM in a mammal, said method comprising normalising tumstatin levels in the tracheal, bronchus and/or bronchiolar tissue of said mammal relative to normal endogenous levels wherein normalising said tumstatin level downregulates tissue remodelling in said tracheal, bronchus and/or bronchiolar tissue.

In yet another aspect, the present invention also provides a method for the treatment and/or prophylaxis of LAM in a mammal, said method comprising normalising the levels of collagen IV α5 chain NC1 domain in the tracheal, bronchus and/or bronchiolar tissue of said mammal relative to normal endogenous levels wherein normalising said collagen IV alpha 5 chain level downregulates tissue remodelling in said tracheal, bronchus and/or bronchiolar tissue.

The present invention also contemplates a pharmaceutical composition comprising the modulatory agent as hereinbefore defined and one or more pharmaceutically acceptable carriers and/or diluents when used in the method of the invention.

Yet another aspect of the present invention is directed to a method for detecting susceptibility to the development of airway tissue remodelling in a mammal, said method comprising screening for the level of tumstatin protein and/or gene expression in said mammal or in an airway tissue derived biological sample from said mammal wherein a decrease in the level of tumstatin relative to the normal endogenous levels of a corresponding sample is indicative of the existence of said susceptibility.

BRIEF DESCRIPTION OF THE DRAWINGS

Embodiments of the invention are described herein, by way of non-limiting example only, with reference to the following drawings.

DETAILED DESCRIPTION OF THE INVENTION

Figure 1:
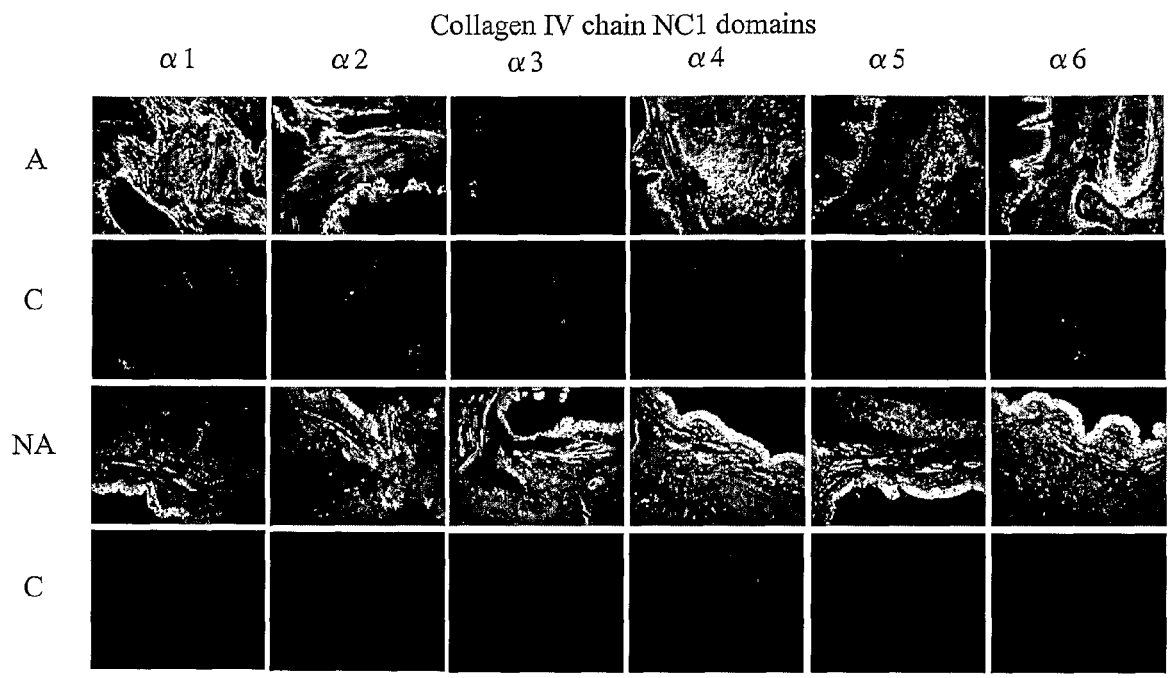
FIG. 1. Images depicting staining for the NC1 domain of the six collagen IV α chains in sections of bronchial rings derived from asthmatic and non-asthmatic subjects. These immunohistochemical images are derived from two different subjects with asthma, and two different non-asthmatic subjects and are representative of all tested (asthma n=5, non-asthma n=4).

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

The articles "a" and "an" are used herein to refer to one or to more than one (i.e., to at least one) of the grammatical object of the article. By way of example, "an element" means one element or more than one element.

As used herein the term "effective amount" includes within its meaning a non-toxic but sufficient amount of an agent or compound to provide the desired effect. The exact amount required will vary from subject to subject depending on factors such as the species being treated, the age and general condition of the subject, the severity of the condition being treated, the particular agent being administered and the mode of administration and so forth. Thus, it is not possible to specify an exact "effective amount". However, for any given case, an appropriate "effective amount" may be determined by one of ordinary skill in the art using only routine experimentation.

As used herein the term "polypeptide" means a polymer made up of amino acids linked together by peptide bonds. The terms "polypeptide" and "protein" are used interchangeably herein, although for the purposes of the present invention a "polypeptide" may constitute a portion of a full length protein. The term "polynucleotide" as used herein refers to a single- or double-stranded polymer of deoxyribonucleotide, ribonucleotide bases or known analogues or natural nucleotides, or mixtures thereof. In some contexts in the present specification the terms "polynucleotide" and "nucleic acid molecule" are used interchangeably.

The subject specification contains amino acid and nucleotide sequence information prepared using the programme Patentin Version 3.1, presented herein after the bibliography. Each amino acid and nucleotide sequence is identified in the sequence listing by the numeric indicator <210> followed by the sequence identifier (e.g. <210>1, <210>2, etc). The length, type of sequence (amino acid, DNA, etc.) and source organism for each sequence is indicated by information provided in the numeric indicator fields <211>, <212> and <213>, respectively. Amino acid and nucleotide sequences referred to in the specification are identified by the indicator SEQ ID NO: followed by the sequence identifier (e.g. SEQ ID NO:1, SEQ ID NO:2, etc.). The sequence identifier referred to in the specification correlates to the information provided in numeric indicator field <400> in the sequence listing, which is followed by the sequence identifier (e.g. <400>1, <400>2, etc). That is SEQ ID NO: 1 as detailed in the specification correlates to the sequence indicated as <400>1 in the sequence listing.

The present invention is predicated, in part, on the determination that endogenous tumstatin levels are downregulated in the airway tissue of patients who are undergoing or predisposed to undergoing airway tissue remodelling. Tissue remodelling is the unwanted and undesirable outcome of some airway diseases such as asthma and LAM. Accordingly, in the absence of the development of cures for these diseases, the development by the present inventors of means to reduce tissue remodelling, by increasing tumstatin levels, is a crucial finding which has enabled the rational design of therapeutic and prophylactic methods for reducing the occurrence or severity of this highly undesirable and irreversible outcome of many airway diseases. The determinations detailed herein have also facilitated the development of means for diagnosing a predisposition to the occurrence of unwanted airway tissue remodelling.

Accordingly, one aspect of the present invention is directed to a method of regulating the occurrence of airway tissue remodelling, said method comprising modulating the level of tumstatin in said airway tissue wherein normalising tumstatin levels in said tissue relative to normal endogenous levels downregulates the occurrence of tissue remodelling and decreasing tumstatin levels in said tissue relative to normal endogenous levels facilitates the occurrence of tissue remodelling.

Alternatively, the method may comprise increasing tumstatin levels above normal endogenous levels in circumstances where this may be appropriate in order, for example, to reduce, prevent, reverse or otherwise retard airway tissue remodelling.

Another aspect of the invention provides a method for improving airway conductance in a subject in need thereof, the method comprising administering to the subject an effective amount of one or more of tumstatin; a derivative, variant or homologue thereof; a polynucleotide encoding tumstatin or a derivative, variant or homologue thereof; or an agent capable of increasing the expression or production of tumstatin.

As detailed herein, and without limiting the present invention to any one theory or mode of action, the present invention is predicated on the determination that tumstatin is expressed endogenously in airway tissue and that a reduction in the normal level of tumstatin in this tissue facilitates the occurrence of tissue remodelling where the relevant stimuli are present. Accordingly, it should be understood that it is thought that tumstatin is not of itself directly involved in the airway tissue remodelling cellular events other than to the extent that it either facilitates or inhibits the occurrence of these events. Still without limiting the present invention in any way, airway tissue remodelling is characterised by a range of cellular events including thickening of the lamina reticularis, an increase in the mass of airway smooth muscle, increased extracellular matrix deposition and an increase in the number of blood vessels. Current therapies for treating airway diseases such as asthma are largely based on down-regulating the inflammatory aspects of these diseases. However, the use of anti-inflammatory drugs, such as corticosteroids, has not been successful in also preventing or reversing the occurrence of airway tissue remodelling. Accordingly, even in patients who are being successfully treated for airway inflammation they nevertheless often undergo airway tissue remodelling, thereby indicating that these two events are not directly linked and that they require separate treatment regimens in order to effect their management.

Reference to regulating the "occurrence" of airway tissue remodelling by modulating tumstatin levels should therefore be understood to mean that said tumstatin may not of itself directly act on the cellular events which are generally understood to constitute "tissue remodelling", although this is not excluded, but may act on a related cellular event which in turn impacts on the progression of one or more tissue remodelling pathologies. For example, and without limiting the present invention in any way, increasing tumstatin levels may act to downregulate airway tissue angiogenesis, the occurrence of said angiogenesis being necessary for certain aspects of one or more tissue remodelling pathologies to occur.

To this end, it should also be understood that reference to "tissue remodelling" is intended as a reference to any one or more of the cellular events and pathological outcomes which constitute the phenomenon of tissue remodelling.

As detailed herein, airway tissue remodelling is not fully understood. However, at the pathological level it is generally understood to encompass one or more of an increase in smooth muscle mass, mucus gland hyperplasia, persistence of chronic inflammatory cellular infiltrates, release of fibrogenic growth factors, collagen deposition, thickening of the lamina reticularis and increased extracellular matrix deposition. Reference to "tissue remodelling" should therefore be understood as reference to any one or more of these events since the range of pathologies which are associated with airway tissue remodelling in the context of one disease condition relative to another may differ. Without limiting the present invention in any way, it is believed that a reduction in angiogenesis which will be achieved by the reintroduction of tumstatin into the asthmatic lung will reverse pathological changes which constitute tissue remodelling.

The tissue remodelling which is regulatable by the method of the present invention is airway tissue remodelling. By "airway tissue" is meant the tissue of the passages which run from the back of the mouth and nose into the lungs, together with the alveoli. The largest of these passages is the trachea (also known as the "windpipe"). In the chest, the trachea divides into two smaller passages termed the bronchi, each of these being further characterised by three regions termed the primary bronchus, secondary bronchus and tertiary bronchus. Each bronchus enters one lung and divides further into narrower passages termed the bronchioles. The terminal bronchiole supplies the alveoli. This network of passages are often colloquially termed the "bronchial tree" and, in the context of asthma, undergo inflammation, muscle constriction and swelling of their lining leading to a reduction in airflow into and out of the lungs. It is this tissue which also ultimately undergoes remodelling, thereby leading to still further complications in terms of the irreversible reduction of lung functioning.

The present invention therefore preferably provides a method of regulating the occurrence of tracheal, bronchus or bronchiolar tissue remodelling, said method comprising modulating the level of tumstatin in said tracheal, bronchus or bronchiolar tissue wherein normalising tumstatin levels in said tissue relative to normal endogenous levels downregulates the occurrence of said tissue remodelling and decreasing tumstatin levels in said tissue relative to normal endogenous levels facilitates the occurrence of said tissue remodelling.

As detailed hereinbefore, the development of the present invention is based on the determination that tumstatin is normally endogenously expressed by airway tissue and that the loss of this expression facilitates airway tissue remodelling to occur. Accordingly, reference to "normal endogenous levels" should be understood as a reference to the level of tumstatin which is expressed in the airway tissue of a subject who is not undergoing nor is predisposed to undergoing airway tissue remodelling. It would be appreciated by the person of skill in the art that this "normal level" is likely to correspond to a range of levels, as opposed to a singularly uniform discrete level, due to differences between cohorts of individuals. By "cohort" is meant a cohort characterised by one or more features which are also characteristic of the subject who is undergoing treatment. These features include, but are not limited to, age, gender or ethnicity, for example. Accordingly, reference herein to modulating tumstatin levels relative to normal endogenous levels is a reference to increasing or decreasing airway tissue tumstatin levels relative to either a discrete tumstatin level which may have been determined for normal individuals who are representative of the same cohort as the individual being treated or relative to a defined tumstatin level range which corresponds to that expressed by a population of individuals corresponding to those from a range of different cohorts.

In terms of modulating tumstatin levels in order to achieve the objective of the present invention, it has been determined that by upregulating airway tissue tumstatin levels in order to approach the normal endogenous levels which have been lost, the incidence of airway tissue remodelling is reduced. This is herein termed "normalising tumstatin levels". To this end, however, it should be understood that the subject tumstatin level need not necessarily be fully normalised in order to achieve the objective of the present invention, although complete normalisation is a preferred embodiment. Merely partially increasing tumstatin levels may effect a decrease in the incidence of airway tissue remodelling, even if not entirely preventing it. This may therefore at least ameliorate the incidence or severity of tissue remodelling in the subject, this also being a highly desirable outcome since it is tantamount to reducing the level of airway tissue scarring, even if not necessarily entirely eliminating it. It should also be understood that the method of the present invention may be applied transiently or in an ongoing manner depending on the requirements of the particular situation. Further, it will be appreciated that there may be circumstances in which it is desirable or beneficial to elevate levels of tumstatin beyond normal endogenous levels. Such elevation of tumstatin levels is contemplated and encompassed by the present application.

As would be appreciated, in the context of therapeutic or prophylactic treatment regimens one is generally seeking to downregulate the occurrence of tissue remodelling in order to minimise this irreversible form of tissue damage. However, in some circumstances it may be desirable to induce or upregulate the occurrence of airway tissue remodelling, for example in an in vitro model or an animal model, in order to facilitate an outcome such as providing a system for screening for the effectiveness of adjunctive therapies, prophylactic therapies or for otherwise facilitating the ongoing analysis of airway tissue remodelling. To this end, one would achieve this outcome by decreasing the endogenous tumstatin levels of the subject airway tissue. Reference to "decreasing" in this regard should be understood to have an analogous meaning to "normalising" in that said decrease may be partial or total and will depend on the extent to which one is seeking to facilitate the occurrence of the airway tissue remodelling event.

Accordingly, in one embodiment the present invention is directed to a method of downregulating the occurrence of airway tissue remodelling, said method comprising normalising tumstatin levels in said tissue relative to normal endogenous levels.

In another embodiment the present invention is directed to a method of upregulating the occurrence of airway tissue remodelling, said method comprising decreasing tumstatin levels in said tissue relative to normal endogenous levels.

Similarly, the present invention contemplates the downregulation, prevention or reversal of airway tissue remodelling in a subject buy administering to the subject an effective amount of one or more of tumstatin; a derivative, variant or homologue thereof; a polynucleotide encoding tumstatin or a derivative, variant or homologue thereof; or an agent capable of increasing the expression or production of tumstatin.

Preferably, said airway tissue is tracheal, bronchus and/or bronchiolar tissue.

It should therefore be understood that the methods of the present invention can be performed either in vitro or in vivo. Although methods are typically to therapeutically or prophylactically treat an individual in vivo in order to preferably downregulate airway tissue remodelling or improve airway conductance, it should nevertheless be understood that it may be desirable that a method of the invention be applied in an in vitro environment, such as in the contexts detailed above.

Accordingly, the present invention provides a method of regulating the occurrence of airway tissue remodelling in a mammal, said method comprising modulating the level of tumstatin in the airway tissue of said mammal wherein normalising tumstatin levels in said tissue relative to normal endogenous levels downregulates the occurrence of tissue remodelling and decreasing tumstatin levels in said tissue relative to normal endogenous levels facilitates the occurrence of tissue remodelling.

Preferably, said airway tissue is tracheal, bronchus or bronchiolar tissue.

Methods of the present invention are predicated on modulating levels of the tumstatin protein. Tumstatin corresponds to the NC1 domain of the α3 chain of the type IV human collagen molecule. It is known to interact with, inter alia, αVβ3 integrin. Reference to "tumstatin" should be understood as a reference to all forms of this molecule and to functional derivatives and homologues thereof. This includes, for example, any isoforms which arise from alternative splicing of the subject tumstatin mRNA or functional mutants or polymorphic variants of these proteins.

"Derivatives" of tumstatin include functional fragments, parts, portions or variants from either natural or non-natural sources. Non-natural sources include, for example, recombinant or synthetic sources. By "recombinant sources" is meant that the cellular source from which the subject molecule is harvested has been genetically altered. This may occur, for example, in order to increase or otherwise enhance the rate and volume of production by that particular cellular source. Parts or fragments include, for example, functionally active regions of the molecule which may be produced by synthetic or recombinant means well known to those skilled in the art. For example suitable derivatives may be peptide fragments such as those set forth in SEQ ID Nos 6 and 7 designated T3 and T7 (Maeshima et al., 2001). Other peptide fragments of tumstatin are also contemplated and fall within the scope of the invention, including but not limited to fragments described in Maeshima et al. 2000 and Maeshima et al., 2001.

The following peptide fragments of tumstatin are functionally active, showing antiangiogenic activity, wherein proliferation of endothelial cells is inhibited:

T3 LQRFTTMPFLFCNVNDVCNF (SEQ ID NO: 6)
T7 TMPFLFCNVNDVCNFASRNDYSYWL (SEQ ID NO: 7)

It can be seen that the sequence TMPFLFCNVNDVCNF (SEQ ID NO:8) is common to both of the foregoing active peptide fragments.

Derivatives may also be derived from insertion, deletion or substitution of amino acids. Amino acid insertional derivatives include amino and/or carboxylic terminal fusions as well as intrasequence insertions of single or multiple amino acids. Insertional amino acid sequence variants are those in which one or more amino acid residues are introduced into a predetermined site in the protein although random insertion is also possible with suitable screening of the resulting product. Deletional variants are characterised by the removal of one or more amino acids from the sequence. Substitutional amino acid variants are those in which at least one residue in a sequence has been removed and a different residue inserted in its place. Additions to amino acid sequences include fusions with other peptides, polypeptides or proteins, as detailed above.

Derivatives also include fragments having particular parts of the protein fused to peptides, polypeptides or other proteinaceous or non-proteinaceous molecules. For example, tumstatin may be fused to a molecule to facilitate its localisation to the airway tissue.

As used herein a "variant" of tumstatin means a molecule which exhibits at least some of the functional activity of the form of tumstatin of which it is a variant. A variant may take any form and may be naturally or non-naturally occurring.

As used herein a "homologue" means that the molecule is derived from a species other than that which is being treated in accordance with the method of the present invention. This may occur, for example, where it is determined that a species other than that which is being treated produces a form of tumstatin which exhibits similar and suitable functional characteristics to that of the tumstatin which is naturally produced by the subject undergoing treatment.

Modulating tumstatin levels may be achieved by any suitable means including, but not limited to:

(i) Modulating absolute levels of tumstatin such that either more or less of tumstatin is present in the airway tissue environment.

(ii) Activating or antagonising tumstatin protein functional activity such that the functional effectiveness of said tumstatin is either increased or decreased. For example, increasing the half life of tumstatin may achieve an increase in the functionally effective level of tumstatin without actually necessitating an increase in the absolute concentration of tumstatin in the airway tissue. Similarly, the partial antagonism of tumstatin may act to reduce, although not necessarily eliminate, the functional effectiveness of said tumstatin.

Accordingly, this may provide a means of down-regulating tumstatin functioning without necessarily down-regulating absolute concentrations of the tumstatin.

In terms of achieving the up or down-regulation of the tumstatin, means for achieving this objective would be well known to the person of skill in the art and include, but are not limited to:

(i) Introducing into a cell a nucleic acid molecule encoding tumstatin in order to up-regulate the capacity of said cell to express tumstatin.

(ii) Introducing into a cell a proteinaceous or non-proteinaceous molecule which modulates transcriptional and/or translational regulation of a gene, wherein this gene may be the tumstatin gene or functional portion thereof or some other gene or gene region (e.g. promoter region) which directly or indirectly modulates the expression of the tumstatin gene.

(iii) Introducing into a cell the tumstatin expression product (this should be understood to include the use of tumstatin homologues).

(iv) Introducing a proteinaceous or non-proteinaceous molecule which functions as an antagonist to the tumstatin expression product.

(v) Introducing a proteinaceous or non-proteinaceous molecule which functions as an agonist of the tumstatin expression product.

The proteinaceous molecules described above may be derived from any suitable source such as natural, recombinant or synthetic sources and includes fusion proteins or molecules which have been identified following, for example, natural product screening. The reference to non-proteinaceous molecules may be, for example, a reference to a nucleic acid molecule or it may be a molecule derived from natural sources, such as for example natural product screening, or may be a chemically synthesised molecule. The present invention also contemplates analogues of the tumstatin expression product or small molecules capable of acting as agonists or antagonists. Chemical agonists may not necessarily be derived from the tumstatin expression product but may share certain conformational similarities. Alternatively, chemical agonists may be specifically designed to meet certain physiochemical properties. Antagonists may be any compound capable of blocking, inhibiting or otherwise preventing tumstatin from carrying out its normal biological function. Antagonists include antibodies, such as monoclonal antibodies, and antisense nucleic acids which prevent transcription or translation of tumstatin genes or mRNA in mammalian cells. Modulation of expression may also be achieved utilising antigens, RNA, ribosomes, DNAzymes, aptamers, antibodies or molecules suitable for use in cosuppression. Suitable antisense oligonucleotide sequences (single stranded DNA fragments) of tumstatin may be created or identified by their ability to suppress the expression of the tumstatin. The production of antisense oligonucleotides for a given protein is described in, for example, Stein and Cohen, 1988 (Cancer Res 48:2659-68) and van der Krol et al., 1988 (Biotechniques 6:958-976).

The proteinaceous and non-proteinaceous molecules referred to in points (i)-(v), above, are herein collectively referred to as "modulatory agents".

Antibodies that selectively bind to tumstatin, as well as fragments and analogues thereof, are encompassed within the scope of modulatory agents. Suitable antibodies include, but are not limited to polyclonal, monoclonal, chimeric, humanised, single chain, Fab fragments, and an Fab expression library. Antibodies may act as agonists or antagonists of tumstatin polypeptides, or fragments or analogues thereof. Preferably antibodies are prepared from discrete regions or fragments of the tumstatin polypeptide. Methods for the generation of suitable antibodies will be readily appreciated by those skilled in the art. For example, an anti-clusterin monoclonal antibody, typically containing may be prepared using the hybridoma technology described in Antibodies—A Laboratory Manual, Harlow and Lane, eds., Cold Spring Harbor Laboratory, N.Y. (1988).

Screening for the modulatory agents hereinbefore defined can be achieved by any one of several suitable methods including, but in no way limited to, contacting a cell comprising the tumstatin gene or functional equivalent or derivative thereof with an agent and screening for the modulation of tumstatin protein production or functional activity, modulation of the expression of a nucleic acid molecule encoding tumstatin or modulation of the activity or expression of a downstream tumstatin cellular target. Detecting such modulation can be achieved utilising techniques such as Western blotting, electrophoretic mobility shift assays and/or the readout of reporters such as luciferases, chloramphenicol acetyltransferase (CAT) and the like.

It should be understood that the tumstatin gene may be naturally occurring in the cell which is the subject of testing or it may have been transfected into a host cell for the purpose of testing. Further, the naturally occurring or transfected gene may be constitutively expressed—thereby providing a model useful for, inter alia, screening for agents which down regulate tumstatin activity, at either the nucleic acid or expression product level, or the gene may require activation—thereby providing a model useful for, inter alia, screening for agents which up-regulate tumstatin expression. Further, to the extent that a tumstatin nucleic acid molecule is transfected into a cell, that molecule may comprise the entire tumstatin gene or it may merely comprise a portion of the gene such as the portion which regulates expression of the tumstatin product. For example, the tumstatin promoter region may be transfected into the cell which is the subject of testing. In this regard, where only the promoter is utilised, detecting modulation of the activity of the promoter can be achieved, for example, by ligating the promoter to a reporter gene. For example, the promoter may be ligated to luciferase or a CAT reporter, the modulation of expression of which gene can be detected via modulation of luminescence intensity or CAT reporter activity, respectively. In another example, the subject of detection could be a downstream tumstatin regulatory target, rather than the tumstatin itself, such as tumstatin/$\alpha V \beta 3$ integrin binding (see for example Sudhakar et al, 2003). Yet another example includes tumstatin binding sites ligated to a minimal reporter. Modulation of tumstatin activity can be detected by screening for the modulation of functional events such as angiogenesis inhibition or apoptosis induction. This is an example of an indirect system where modulation of tumstatin expression, per se, is not the subject of detection. Rather, modulation of the down-stream activity which tumstatin regulates is monitored.

These methods provide a mechanism for performing high throughput screening of putative modulatory agents such as the proteinaceous or non-proteinaceous agents comprising synthetic, combinatorial, chemical and natural libraries. These methods will also facilitate the detection of agents which bind either the tumstatin nucleic acid molecule or expression product itself or which modulate the expression of an upstream molecule, which upstream molecule subsequently modulates tumstatin expression or expression product activity. Accordingly, these methods provide a mechanism of detecting agents which either directly or indirectly modulate tumstatin expression and/or activity.

The agents which are utilised in accordance with the method of the present invention may take any suitable form. For example, proteinaceous agents may be glycosylated or unglycosylated, phosphorylated or dephosphorylated to various degrees and/or may contain a range of other molecules fused, linked, bound or otherwise associated with the proteins such as amino acids, lipid, carbohydrates or other peptides, polypeptides or proteins. Similarly, the subject non-proteinaceous molecules may also take any suitable form. Both the proteinaceous and non-proteinaceous agents herein described may be linked, bound otherwise associated with any other proteinaceous or non-proteinaceous molecules. For example, in one embodiment of the present invention said agent is associated with a molecule which permits its targeting to the tissue of the airways.

The subject proteinaceous or non-proteinaceous molecule may act either directly or indirectly to modulate the expression of tumstatin or the activity of the tumstatin expression product. Said molecule acts directly if it associates with the tumstatin nucleic acid molecule or expression product to modulate expression or activity, respectively. Said molecule acts indirectly if it associates with a molecule other than the tumstatin nucleic acid molecule or expression product which other molecule either directly or indirectly modulates the expression or activity of the tumstatin nucleic acid molecule or expression product, respectively.

The term "expression" refers interchangeably to expression of a polypeptide or protein and expression of a polynucleotide or gene. Accordingly, included within the scope of the term "expression" is the transcription and translation of a polynucleotide. Expression of a polynucleotide may be determined, for example, by measuring the production of messenger RNA (mRNA) transcript levels. Expression of a protein or polypeptide may be determined, for example, by immunoassay using an antibody(ies) that bind with the polypeptide. Reference to "expression product" is a reference to the product produced from the transcription and translation of a nucleic acid molecule. Reference to "modulation" should be understood as a reference to upregulation or downregulation of expression. The term "production" as used herein in relation to tumstatin refers to the generation of the tumstatin protein molecule from the encoding nucleic acid molecule(s). Accordingly, the terms "expression" and "production" may at least in some circumstances be used interchangeably.

Chemical and functional equivalents of tumstatin may also be utilised in methods of the invention. Such equivalents should be understood as molecules exhibiting any one or more of the functional activities of the subject molecule, which functional equivalents may be derived from any source such as being chemically synthesised or identified via screening processes such as natural product screening. For example chemical or functional equivalents can be designed and/or identified utilising well known methods such as combinatorial chemistry or high throughput screening of recombinant libraries or following natural product screening. Antagonistic agents can also be screened for utilising such methods.

For example, libraries containing small organic molecules may be screened, wherein organic molecules having a large number of specific parent group substitutions are used. A general synthetic scheme may follow published methods (e.g., Bunin, et al. (1994) Proc. Natl. Acad. Sci. USA, 91:4708-4712; DeWitt, et al. (1993) Proc. Natl. Acad. Sci. USA, 90:6909-6913). Briefly, at each successive synthetic step, one of a plurality of different selected substituents is added to each of a selected subset of tubes in an array, with the selection of tube subsets being such as to generate all possible permutation of the different substituents employed in producing the library. One suitable permutation strategy is outlined in U.S. Pat. No. 5,763,263.

There is currently widespread interest in using combinational libraries of random organic molecules to search for biologically active compounds (see for example U.S. Pat. No. 5,763,263). Ligands discovered by screening libraries of this type may be useful in mimicking or blocking natural ligands or interfering with the naturally occurring ligands of a biological target. In the present context, for example, they may be used as a starting point for developing tumstatin analogues which exhibit properties such as more potent pharmacological effects. Tumstatin or a functional part thereof may, according to the present invention, be used in combination libraries formed by various solid-phase or solution-phase synthetic methods (see for example U.S. Pat. No. 5,763,263 and references cited therein). By use of techniques, such as that disclosed in U.S. Pat. No. 5,753,187, millions of new chemical and/or biological compounds may be routinely screened in less than a few weeks. Of the large number of compounds identified, only those exhibiting appropriate biological activity are further analysed.

With respect to high throughput library screening methods, oligomeric or small-molecule library compounds capable of interacting specifically with a selected biological agent, such as a biomolecule, a macromolecule complex, or cell, are screened utilising a combinational library device which is easily chosen by the person of skill in the art from the range of well-known methods, such as those described above. In such a method, each member of the library is screened for its ability to interact specifically with the selected agent. In practising the method, a biological agent is drawn into compound-containing tubes and allowed to interact with the individual library compound in each tube. The interaction is designed to produce a detectable signal that can be used to monitor the presence of the desired interaction. Preferably, the biological agent is present in an aqueous solution and further conditions are adapted depending on the desired interaction. Detection may be performed for example by any well-known functional or non-functional based method for the detection of substances.

In addition to screening for molecules which mimic the activity of tumstatin one may identify and utilise molecules which function agonistically or antagonistically to tumstatin in order to up or down-regulate the functional activity of tumstatin in relation to modulating airway tissue remodelling. The use of such molecules is described in more detail below. To the extent that the subject molecule is proteinaceous, it may be derived, for example, from natural or recombinant sources including fusion proteins or following, for example, the screening methods described earlier. The non-proteinaceous molecule may be, for example, a chemical or synthetic molecule which has also been identified or generated in accordance with the methodology identified above. Accordingly, the present invention contemplates the use of chemical analogues of tumstatin capable of acting as agonists or antagonists. Chemical agonists may not necessarily be derived from tumstatin but may share certain conformational similarities. Alternatively, chemical agonists may be specifically designed to mimic certain physiochemical properties of tumstatin. Antagonists may be any compound capable of blocking, inhibiting or otherwise preventing tumstatin from carrying out its normal biological functions. Antagonists include monoclonal antibodies specific for tumstatin or parts of tumstatin.

Analogues of tumstatin or tumstatin agonistic or antagonistic agents contemplated herein include, but are not limited to, modifications to side chains, incorporating unnatural amino acids and/or derivatives during peptide, polypeptide or protein synthesis and the use of crosslinkers and other methods which impose conformational constraints on the analogues. The specific form which such modifications can take will depend on whether the subject molecule is proteinaceous or non-proteinaceous. The nature and/or suitability of a particular modification can be routinely determined by the person of skill in the art.

For example, examples of side chain modifications contemplated by the present invention include modifications of amino groups such as by reductive alkylation by reaction with an aldehyde followed by reduction with NaBH$_4$; amidination with methylacetimidate; acylation with acetic anhydride; carbamoylation of amino groups with cyanate; trinitrobenzylation of amino groups with 2,4,6-trinitrobenzene sulphonic acid (TNBS); acylation of amino groups with succinic anhydride and tetrahydrophthalic anhydride; and pyridoxylation of lysine with pyridoxal-5-phosphate followed by reduction with NaBH$_4$.

The guanidine group of arginine residues may be modified by the formation of heterocyclic condensation products with reagents such as 2,3-butanedione, phenylglyoxal and glyoxal.

The carboxyl group may be modified by carbodiimide activation via O-acylisourea formation followed by subsequent derivatisation, for example, to a corresponding amide.

Sulphydryl groups may be modified by methods such as carboxymethylation with iodoacetic acid or iodoacetamide; performic acid oxidation to cysteic acid; formation of a mixed disulphides with other thiol compounds; reaction with maleimide, maleic anhydride or other substituted maleimide; formation of mercurial derivatives using 4-chloromercuribenzoate, 4-chloromercuriphenylsulphonic acid, phenylmercury chloride, 2-chloromercuri-4-nitrophenol and other mercurials; carbamoylation with cyanate at alkaline pH.

Tryptophan residues may be modified by, for example, oxidation with N-bromosuccinimide or alkylation of the indole ring with 2-hydroxy-5-nitrobenzyl bromide or sulphenyl halides. Tyrosine residues on the other hand, may be altered by nitration with tetranitromethane to form a 3-nitrotyrosine derivative.

Modification of the imidazole ring of a histidine residue may be accomplished by alkylation with iodoacetic acid derivatives or N-carboethoxylation with diethylpyrocarbonate.

Examples of incorporating unnatural amino acids and derivatives during protein synthesis include, but are not limited to, use of norleucine, 4-amino butyric acid, 4-amino-3-hydroxy-5-phenylpentanoic acid, 6-aminohexanoic acid, t-butylglycine, norvaline, phenylglycine, ornithine, sarcosine, 4-amino-3-hydroxy-6-methylheptanoic acid, 2-thienyl alanine and/or D-isomers of amino acids. A list of unnatural amino acids contemplated herein is shown in Table 1.

TABLE 1

| Non-conventional amino acid | Code |
| --- | --- |
| α-aminobutyric acid | Abu |
| α-amino-α-methylbutyrate | Mgabu |
| aminocyclopropane-carboxylate | Cpro |
| aminoisobutyric acid | Aib |
| aminonorbornyl-carboxylate | Norb |
| cyclohexylalanine | Chexa |
| cyclopentylalanine | Cpen |
| D-alanine | Dal |
| D-arginine | Darg |
| D-aspartic acid | Dasp |
| D-cysteine | Dcys |

TABLE 1-continued

| Non-conventional amino acid | Code |
| --- | --- |
| D-glutamine | Dgln |
| D-glutamic acid | Dglu |
| D-histidine | Dhis |
| D-isoleucine | Dile |
| D-leucine | Dleu |
| D-lysine | Dlys |
| D-methionine | Dmet |
| D-ornithine | Dorn |
| D-phenylalanine | Dphe |
| D-proline | Dpro |
| D-serine | Dser |
| D-threonine | Dthr |
| D-tryptophan | Dtrp |
| D-tyrosine | Dtyr |
| D-valine | Dval |
| D-α-methylalanine | Dmala |
| D-α-methylarginine | Dmarg |
| D-α-methylasparagine | Dmasn |
| D-α-methylaspartate | Dmasp |
| D-α-methylcysteine | Dmcys |
| D-α-methylglutamine | Dmgln |
| D-α-methylhistidine | Dmhis |
| D-α-methylisoleucine | Dmile |
| D-α-methylleucine | Dmleu |
| D-α-methyllysine | Dmlys |
| D-α-methylmethionine | Dmmet |
| D-α-methylornithine | Dmorn |
| D-α-methylphenylalanine | Dmphe |
| D-α-methylproline | Dmpro |
| D-α-methylserine | Dmser |
| D-α-methylthreonine | Dmthr |
| D-α-methyltryptophan | Dmtrp |
| D-α-methyltyrosine | Dmty |
| D-α-methylvaline | Dmval |
| D-N-methylalanine | Dnmala |
| D-N-methylarginine | Dnmarg |
| D-N-methylasparagine | Dnmasn |
| D-N-methylaspartate | Dnmasp |
| D-N-methylcysteine | Dnmcys |
| D-N-methylglutamine | Dnmgln |
| D-N-methylglutamate | Dnmglu |
| D-N-methylhistidine | Dnmhis |
| D-N-methylisoleucine | Dnmile |
| D-N-methylleucine | Dnmleu |
| D-N-methyllysine | Dnmlys |
| N-methylcyclohexylalanine | Nmchexa |
| D-N-methylornithine | Dnmorn |
| N-methylglycine | Nala |
| N-methylaminoisobutyrate | Nmaib |
| N-(1-methylpropyl)glycine | Nile |
| N-(2-methylpropyl)glycine | Nleu |
| D-N-methyltryptophan | Dnmtrp |
| D-N-methyltyrosine | Dnmtyr |
| D-N-methylvaline | Dnmval |
| γ-aminobutyric acid | Gabu |
| L-t-butylglycine | Tbug |
| L-ethylglycine | Etg |
| L-homophenylalanine | Hphe |
| L-α-methylarginine | Marg |
| L-α-methylaspartate | Masp |
| L-α-methylcysteine | Mcys |
| L-α-methylglutamine | Mgln |
| L-α-methylhistidine | Mhis |
| L-α-methylisoleucine | Mile |
| L-α-methylleucine | Mleu |
| L-α-methylmethionine | Mmet |
| L-α-methylnorvaline | Mnva |
| L-α-methylphenylalanine | Mphe |
| L-α-methylserine | Mser |
| L-α-methyltryptophan | Mtrp |
| L-α-methylvaline | Mval |
| N-(N-(2,2-diphenylethyl)-carbamylmethyl)glycine | Nnbhm |
| 1-carboxy-1-(2,2-diphenyl-ethylamino)cyclopropane | Nmbc |
| L-N-methylalanine | Nmala |
| L-N-methylarginine | Nmarg |

TABLE 1-continued

| Non-conventional amino acid | Code |
|---|---|
| L-N-methylasparagine | Nmasn |
| L-N-methylaspartic acid | Nmasp |
| L-N-methylcysteine | Nmcys |
| L-N-methylglutamine | Nmgln |
| L-N-methylglutamic acid | Nmglu |
| L-N-methylhistidine | Nmhis |
| L-N-methylisolleucine | Nmile |
| L-N-methylleucine | Nmleu |
| L-N-methyllysine | Nmlys |
| L-N-methylmethionine | Nmmet |
| L-N-methylnorleucine | Nmnle |
| L-N-methylnorvaline | Nmnva |
| L-N-methylornithine | Nmorn |
| L-N-methylphenylalanine | Nmphe |
| L-N-methylproline | Nmpro |
| L-N-methylserine | Nmser |
| L-N-methylthreonine | Nmthr |
| L-N-methyltryptophan | Nmtrp |
| L-N-methyltyrosine | Nmtyr |
| L-N-methylvaline | Nmval |
| L-N-methylethylglycine | Nmetg |
| L-N-methyl-t-butylglycine | Nmtbug |
| L-norleucine | Nle |
| L-norvaline | Nva |
| α-methyl-aminoisobutyrate | Maib |
| α-methyl--aminobutyrate | Mgabu |
| α-methylcyclohexylalanine | Mchexa |
| α-methylcylcopentylalanine | Mcpen |
| α-methyl-α-napthylalanine | Manap |
| α-methylpenicillamine | Mpen |
| N-(4-aminobutyl)glycine | Nglu |
| N-(2-aminoethyl)glycine | Naeg |
| N-(3-aminopropyl)glycine | Norn |
| N-amino-α-methylbutyrate | Nmaabu |
| α-napthylalanine | Anap |
| N-benzylglycine | Nphe |
| N-(2-carbamylethyl)glycine | Ngln |
| N-(carbamylmethyl)glycine | Nasn |
| N-(2-carboxyethyl)glycine | Nglu |
| N-(carboxymethyl)glycine | Nasp |
| N-cyclobutylglycine | Ncbut |
| N-cycloheptylglycine | Nchep |
| N-cyclohexylglycine | Nchex |
| N-cyclodecylglycine | Ncdec |
| N-cylcododecylglycine | Ncdod |
| N-cyclooctylglycine | Ncoct |
| N-cyclopropylglycine | Ncpro |
| N-cycloundecylglycine | Ncund |
| N-(2,2-diphenylethyl)glycine | Nbhm |
| N-(3,3-diphenylpropyl)glycine | Nbhe |
| N-(3-guanidinopropyl)glycine | Narg |
| N-(1-hydroxyethyl)glycine | Nthr |
| N-(hydroxyethyl))glycine | Nser |
| N-(imidazolylethyl))glycine | Nhis |
| N-(3-indolylyethyl)glycine | Nhtrp |
| N-methyl-γ-aminobutyrate | Nmgabu |
| D-N-methylmethionine | Dnmmet |
| N-methylcyclopentylalanine | Nmcpen |
| D-N-methylphenylalanine | Dnmphe |
| D-N-methylproline | Dnmpro |
| D-N-methylserine | Dnmser |
| D-N-methylthreonine | Dnmthr |
| N-(1-methylethyl)glycine | Nval |
| N-methyla-napthylalanine | Nmanap |
| N-methylpenicillamine | Nmpen |
| N-(p-hydroxyphenyl)glycine | Nhtyr |
| N-(thiomethyl)glycine | Ncys |
| penicillamine | Pen |
| L-α-methylalanine | Mala |
| L-α-methylasparagine | Masn |
| L-α-methyl-t-butylglycine | Mtbug |
| L-methylethylglycine | Metg |
| L-α-methylglutamate | Mglu |
| L-α-methylhomophenylalanine | Mhphe |
| N-(2-methylthioethyl)glycine | Nmet |
| L-α-methyllysine | Mlys |
| L-α-methylnorleucine | Mnle |
| L-α-methylornithine | Morn |
| L-α-methylproline | Mpro |
| L-α-methylthreonine | Mthr |
| L-α-methyltyrosine | Mtyr |
| L-N-methylhomophenylalanine | Nmhphe |
| N-(N-(3,3-diphenylpropyl)-carbamylmethyl)glycine | Nnbhe |

Crosslinkers can be used, for example, to stabilise 3D conformations, using homo-bifunctional crosslinkers such as the bifunctional imido esters having $(CH_2)_n$ spacer groups with n=1 to n=6, glutaraldehyde, N-hydroxysuccinimide esters and hetero-bifunctional reagents which usually contain an amino-reactive moiety such as N-hydroxysuccinimide and another group specific-reactive moiety.

As detailed earlier, modulation of tumstatin functional levels may be achieved via the administration of tumstatin, a nucleic acid molecule encoding tumstatin or an agent which effects modulation of tumstatin activity or tumstatin gene expression (herein collectively referred to as "modulatory agents").

In one embodiment, modulation of the expression of tumstatin is achieved by directly affecting expression of tumstatin. Preferably, the introduction of a construct with the gene encoding tumstatin will allow for modulation of the levels of tumstatin upon expression and thereby affect the biological functions for which it is directed.

Without limiting the present invention to any one theory or mode of action, any cell can accept a gene or gene construct encoding tumstatin. However, ideally, the cell can readily accept a gene construct and fully integrate it into the cell to have an influence on the biological function or its own function as well as adjoining cells and cellular environment.

The gene for tumstatin may be obtained, for example, by PCR amplification of mRNA from human (or other species) tissues using tumstatin specific primers and inserted into a mammalian expression vector such as pcDNA3.1 (Clontech) to form a construct or vector that may be transfected into the cell to express tumstatin.

Preferably, a gene sequence for tumstatin is operably linked to a regulatory sequence which is capable of providing for the expression of the coding sequence by a cell. The term "operably linked" refers to a juxtaposition wherein the components described are in a relationship permitting them to function in their intended manner. A regulatory sequence "operably linked" to a coding sequence is ligated in such a way that expression of the coding sequence is achieved under conditions compatible with the control sequences.

While operably linked nucleic acid sequences can be contiguous and in the same reading frame, certain genetic elements e.g. repressor genes may not be contiguously linked to the coding sequence but may still control transcription/translation of the coding sequence.

The term "regulatory sequence(s)" includes promoters and enhancers and other expression regulation signals. These may be selected to be compatible with the cell for which the expression vector is designed. Mammalian promoters, such as β-actin promoters and the myosin light chain promoter may be used. However, other promoters may be adopted to achieve the same effect. These alternate promoters are generally familiar to the skilled addressee. Mammalian promoters also include the metallothionein promoter which can upregulate expression in response to heavy metals such as cadmium and is thus an inducible promoter. Tissue-specific promoters may be used. Viral promoters may also be used, for example the Moloney murine leukaemia virus long terminal repeat (MML V L TR), the promoter rous sarcoma virus (RSV) L TR promoter, the SV40 promoter, the human cytomegalovirus (CMV) IE promoter, herpes simplex virus promoters or adenovirus promoters. All these promoters are readily available in the art.

Such vectors may be transfected into a suitable cell in which the biological function is desired to provide for expression of a polypeptide encoding tumstatin which can then regulate the occurrence of airway tissue remodelling.

The vectors may be, for example, plasmid, virus or phage vectors provided with an origin of replication, optionally a promoter for the expression of the follistatin isoform and optionally a regulator of the promoter. The vectors may contain one or more selectable marker genes for example an ampicillin resistance gene in the case of a bacterial plasmid or a neomycin resistance gene for a mammalian vector. Vectors may be used in vitro, for example for the production of RNA or used to transfect or transform a host cell. The vector may also be adapted to be used in vivo.

The cells in which the vector is transfected are expected to provide for such post-translational modifications as may be needed to confer optimal biological activity on the recombinant tumstatin.

The vector may be transfected into the cell by any means available to the skilled addressee. Preferably, the vector is introduced by calcium phosphate precipitation, electroporation, biolistics (particle bombardment), lipofection, naked DNA, DEAE Dextran or adenoviral or retroviral infection. However, this invention is not restricted to these methods.

If the vector is to be introduced into a germ line to establish a transgenic line, then the transgene may be introduced using anyone of, but not limited to, i) pronuclear microinjection of DNA into a zygote; ii) transfection of preimplantation embryos with recombinant retroviruses carrying the gene of interest; iii) gene transfer into embryonic stem cells by using calcium phosphate-mediated DNA transformation, electroporation, retroviral infection or lipofection; iv) intracytoplasmic coinjection of unfertilized mouse oocytes with exogenous DNA and sperm heads whose membranes had been disrupted. Preferably, pronuclear microinjection is adopted.

Modulation of tumstatin to modulate tissue remodelling events may be achieved by inducing expression of tumstatin by transfection of a construct containing tumstatin under the influence of a promoter or by overexpressing the gene in the cell. By introduction of exogenous tumstatin or a construct to express exogenous tumstatin, the ability of tumstatin to modulate tissue remodelling may be achieved.

The cells are preferably transfected with tumstatin by any means that introduces the tumstatin gene to the cell. Preferably, the gene encoding tumstatin is transfected into the cell via an expression vector by methods routinely available to the skilled addressee or as described above.

Preferably a construct of tumstatin is introduced or transfected into the cell to increase the expression the of tumstatin. Increasing the expression may be achieved by any means known to the skilled addressee including the induction of promoters in the construct. Vectors may be used with regulatory regions that respond to tetracycline, mifepristone or ecdysone.

However, the expression and/or activity of tumstatin may also be increased by indirect methods of targeting including regulators to upregulate gene expression. These regulators may act on the promoters that cause expression of the gene.

Regulation of tumstatin gene expression may generally be achieved by the use of molecules reacting with the promoter of the gene or with a promoter of a nuclear factor regulating the gene, or by RNA processing including splicing and degradation. The activity of proteins themselves may also be targeted by phosphorylation, or allosteric regulation or regulation of the protein degradation such as by the use of protease inhibitors.

Increased expression and/or activity of tumstatin may be achieved by any means that can increase endogeneous tumstatin expression and/or activity thereby resulting in the downregulation of airway tissue remodelling.

As detailed hereinbefore, a further aspect of the present invention relates to the use of the invention in relation to the treatment and/or prophylaxis of disease conditions or other unwanted conditions.

The present invention therefore contemplates a method for the treatment and/or prophylaxis of a condition characterised by aberrant or otherwise unwanted airway tissue remodelling in a mammal, said method comprising modulating the level of tumstatin in the airway tissue of said mammal wherein normalising tumstatin levels in said tissue relative to normal endogenous levels downregulates the occurrence of tissue remodelling and decreasing tumstatin levels in said tissue relative to normal endogenous levels facilitates the occurrence of tissue remodelling.

Reference to "aberrant or otherwise unwanted tissue remodelling" should be understood as a reference to either the unwanted presence or absence of tissue remodelling, per se, or the unwanted degree of tissue remodelling which is or is likely to occur. As detailed hereinbefore, although the preferred method is to prevent the occurrence of tissue remodelling in the context of airway disease conditions such as asthma and LAM, there may be some circumstances in which it is desirable to upregulate or induce the occurrence of airway tissue remodelling. By way of example, it may be desirable to upregulate tissue remodelling during the process of wound repair. Many infectious pathogens (e.g. bacteria) will induce local lesions in the lungs, and, to accelerate the healing process it may be desirable to upregulate tissue remodelling. Upregulation may also be desirable in bronchiectasis.

The present invention therefore more particularly provides a method for the treatment and/or prophylaxis of a condition characterised by unwanted airway tissue remodelling in a mammal, said method comprising normalising tumstatin levels in said tissue relative to normal endogenous levels wherein normalising said tumstatin level downregulates said airway tissue remodelling.

Most particularly, said airway tissue is tracheal, bronchus and/or bronchiolar tissue.

Preferably, said condition is asthma, LAM, or any lung condition where angiogenesis is present, e.g. pulmonary fibrosis, Chronic Obstructive Pulmonary Disease (COPD), Cystic Fibrosis.

Accordingly, in one preferred embodiment there is provided a method for the treatment and/or prophylaxis of asthma in a mammal, said method comprising normalising tumstatin levels in the tracheal, bronchus and/or bronchiolar tissue of said mammal relative to normal endogenous levels wherein normalising said tumstatin level downregulates tissue remodelling in said tracheal, bronchus and/or bronchiolar tissue.

In another preferred embodiment there is provided a method for the treatment and/or prophylaxis of LAM in a mammal, said method comprising normalising tumstatin levels in the tracheal, bronchus and/or bronchiolar tissue of said mammal relative to normal endogenous levels wherein normalising said tumstatin level downregulates tissue remodelling in said tracheal, bronchus and/or bronchiolar tissue.

This aspect of the present invention is preferably achieved by administering to said mammal an effective amount of a modulatory agent as hereinbefore defined. To this end, an "effective amount" means an amount necessary to at least partly attain the desired response, or to delay the onset or inhibit progression or halt altogether, the onset or progression of the particular condition being treated. The amount varies depending upon the health and physical condition of the individual to be treated, the taxonomic group of the individual to be treated, the degree of protection desired, the formulation of the composition, the assessment of the medical situation, and other relevant factors. It is expected that the amount will fall in a relatively broad range that can be determined through routine trials.

In work leading to the present invention and described in the Examples hereafter, it has been demonstrated that in LAM patients, the levels of both tumstatin (or collagen IV α3 chain NC1 domain) and collagen IV α5 chain NC1 domain are decreased. Accordingly, in yet another aspect, the present invention also provides a method for the treatment and/or prophylaxis of LAM in a mammal, said method comprising normalising the levels of collagen IV α5 chain NC1 domain in the tracheal, bronchus and/or bronchiolar tissue of said mammal relative to normal endogenous levels wherein normalising said collagen IV α5 chain NC1 domain level downregulates tissue remodelling in said tracheal, bronchus and/or bronchiolar tissue.

Reference herein to "treatment" and "prophylaxis" is to be considered in its broadest context. The term "treatment" does not necessarily imply that a subject is treated until total recovery. This is a particularly significant point in relation to the present invention since in the context of some disease conditions, such as asthma, the method of the present invention is "treating" the disease condition in terms of reducing or eliminating the occurrence of a highly undesirable and irreversible outcome of the progression of the conditions but may not of itself prevent the initial occurrence of the disease, for example the occurrence of an asthma attack. Similarly, "prophylaxis" does not necessarily mean that the subject will not eventually contract a disease condition. Accordingly, treatment and prophylaxis include amelioration of the symptoms of a particular condition or preventing or otherwise reducing the risk of developing a particular condition. The term "prophylaxis" may be considered as reducing the severity or onset of a particular condition. "Treatment" may also reduce the severity of an existing condition.

The present invention further contemplates a combination of therapies, such as the administration of the modulatory agent together with other proteinaceous or non-proteinaceous molecules which may facilitate the desired therapeutic or prophylactic outcome. For example, in the context of asthma, one may seek to maintain ongoing anti-inflammatory therapies in order to control the incidence of inflammation.

Administration of molecules of the present invention hereinbefore described [herein collectively referred to as "modulatory agents"], in the form of a pharmaceutical composition, may be performed by any convenient means. The modulatory agent of the pharmaceutical composition is contemplated to exhibit therapeutic activity when administered in an amount which depends on the particular case. The variation depends, for example, on the human or animal and the modulatory agent chosen. A broad range of doses may be applicable. Considering a patient, for example, from about 0.1 mg to about 1 mg of modulatory agent may be administered per kilogram of body weight per day. Dosage regimens may be adjusted to provide the optimum therapeutic response. For example, several divided doses may be administered daily, weekly, monthly or other suitable time intervals or the dose may be proportionally reduced as indicated by the exigencies of the situation.

The modulatory agent may be administered in any convenient or suitable manner such as by intravenous, oral or respiratory routes. Preferably, the modulatory agent is administered by the respiratory route. The modulatory agent may be administered in the form of pharmaceutically acceptable non-toxic salts, such as acid addition salts or metal complexes, e.g. with zinc, iron or the like (which are considered as salts for purposes of this application). Illustrative of such acid addition salts are hydrochloride, hydrobromide, sulphate, phosphate, maleate, acetate, citrate, benzoate, succinate, malate, ascorbate, tartrate and the like. If the active ingredient is to be administered in tablet form, the tablet may contain a binder such as tragacanth, corn starch or gelatin; a disintegrating agent, such as alginic acid; and a lubricant, such as magnesium stearate.

In accordance with these methods, the agent defined in accordance with the present invention may be coadministered with one or more other compounds or molecules. By "coadministered" is meant simultaneous administration in the same formulation or in two different formulations via the same or different routes or sequential administration by the same or different routes. For example, the subject tumstatin may be coadministered together with anti-inflammatory or other relevant drugs in the context of asthma treatment. By "sequential" administration is meant a time difference of from seconds, minutes, hours or days between the administration of the two types of molecules. These molecules may be administered in any order.

Another aspect of the present invention relates to the use of an agent capable of modulating the level of tumstatin in the airway tissue of a mammal in the manufacture of a medicament for the regulation of airway tissue remodelling in said mammal wherein normalising tumstatin levels in said tissue relative to normal endogenous levels downregulates the occurrence of tissue remodelling and decreasing tumstatin levels in said tissue relative to normal endogenous levels facilitates the occurrence of tissue remodelling.

In still another aspect the present invention relates to the use of an agent capable of modulating the level of tumstatin in the airway tissue of a mammal in the manufacture of a medicament for the treatment of a condition characterised by aberrant or otherwise unwanted airway tissue remodelling wherein normalising tumstatin levels in said tissue relative to normal endogenous levels downregulates the occurrence of tissue remodelling and decreasing tumstatin levels in said tissue relative to normal endogenous levels facilitates the occurrence of tissue remodelling.

Preferably, said condition is characterised by unwanted airway tissue remodelling and more preferably said condition is asthma or LAM.

In accordance with these aspects of the present invention, said airway tissue is preferably tracheal, bronchus or bronchiolar tissue.

The terms "mammal" and "subject" as used herein include humans, primates, livestock animals (e.g. sheep, pigs, cattle, horses, donkeys), laboratory test animals (e.g. mice, rabbits, rats, guinea pigs), companion animals (e.g. dogs, cats) and captive wild animals (e.g. foxes, kangaroos, deer). Preferably, the mammal is human or a laboratory test animal. Even more preferably, the mammal is a human.

In yet another further aspect, the present invention contemplates a pharmaceutical composition comprising the modulatory agent as hereinbefore defined and one or more pharmaceutically acceptable carriers and/or diluents when used in the method of the invention. Said agents are referred to as the active ingredients.

Suitable compositions may be prepared according to methods which are known to those of ordinary skill in the art and may include a pharmaceutically acceptable diluent, adjuvant and/or excipient. The diluents, adjuvants and excipients must be "acceptable" in terms of being compatible with the other ingredients of the composition, and not deleterious to the recipient thereof. The diluent, adjuvant or excipient may be a solid or a liquid, or both, and may be formulated with the compound as a unit-dose, for example, a tablet, which may contain from 0.5% to 59% by weight of the active compound, or up to 100% by weight of the active compound. One or more active compounds may be incorporated in the formulations of the invention, which may be prepared by any of the well known techniques of pharmacy consisting essentially of admixing the components, optionally including one or more accessory ingredients.

Examples of pharmaceutically acceptable diluents are demineralised or distilled water; saline solution; vegetable based oils such as peanut oil, safflower oil, olive oil, cottonseed oil, maize oil, sesame oils such as peanut oil, safflower oil, olive oil, cottonseed oil, maize oil, sesame oil, arachis oil or coconut oil; silicone oils, including polysiloxanes, such as methyl polysiloxane, phenyl polysiloxane and methylphenyl polysolpoxane; volatile silicones; mineral oils such as liquid paraffin, soft paraffin or squalane; cellulose derivatives such as methyl cellulose, ethyl cellulose, carboxymethylcellulose, sodium carboxymethylcellulose or hydroxypropylmethylcellulose; lower alkanols, for example ethanol or iso-propanol; lower aralkanols; lower polyalkylene glycols or lower alkylene glycols, for example polyethylene glycol, polypropylene glycol, ethylene glycol, propylene glycol, 1,3-butylene glycol or glycerin; fatty acid esters such as isopropyl palmitate, isopropyl myristate or ethyl oleate; polyvinylpyrridone; agar; carrageenan; gum tragacanth or gum acacia, and petroleum jelly. Typically, the carrier or carriers will form from 1% to 99.9% by weight of the compositions.

Administration of compositions of the invention may be achieved by any standard route, including intracavitary, intravesical, intramuscular, intraarterial, intravenous, intraocular, subcutaneous, topical or oral. For example, in circumstances where it is required that appropriate concentrations of the desired compound are delivered directly to the site in the body to be treated, administration may be regional rather than systemic. Regional administration provides the capability of delivering very high local concentrations of the desired compound to the required site and thus is suitable for achieving the desired therapeutic or preventative effect whilst avoiding exposure of other organs of the body to the compound and thereby potentially reducing side effects.

The pharmaceutical forms suitable for injectable use include sterile aqueous solutions (where water soluble) or dispersions and sterile powders for the extemporaneous preparation of sterile injectable solutions or dispersion or may be in the form of a cream or other form suitable for topical application. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of superfactants. The preventions of the action of microorganisms can be brought about by various antibacterial and antifungal agents, for example, parabens, chlorobutanol, phenol, sorbic acid, thimerosal and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilisation. Generally, dispersions are prepared by incorporating the various sterilised active ingredient into a sterile vehicle which contains the basic dispersion medium and the required other ingredients from those enumerated above. In the case of sterile powders for the preparation of sterile injectable solutions, the preferred methods of preparation are vacuum drying and the freeze-drying technique which yield a powder of the active ingredient plus any additional desired ingredient from previously sterile-filtered solution thereof.

When the active ingredients are suitably protected they may be orally administered, for example, with an inert diluent or with an assimilable edible carrier, or it may be enclosed in hard or soft shell gelatin capsule, or it may be compressed into tablets, or it may be incorporated directly with the food of the diet. For oral therapeutic administration, the active compound may be incorporated with excipients and used in the form of ingestible tablets, buccal tablets, troches, capsules, elixirs, suspensions, syrups, wafers, and the like. Such compositions and preparations should contain at least 1% by weight of active compound. The percentage of the compositions and preparations may, of course, be varied and may conveniently be between about 5 to about 80% of the weight of the unit. The amount of active compound in such therapeutically useful compositions in such that a suitable dosage will be obtained. Preferred compositions or preparations according to the present invention are prepared so that an oral dosage unit form contains between about 0.1 µg and 2000 mg of active compound.

The tablets, troches, pills, capsules and the like may also contain the components as listed hereafter: a binder such as gum, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin may be added or a flavouring agent such as peppermint, oil of wintergreen, or cherry flavouring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparabens as preservatives, a dye and flavouring such as cherry or orange flavour. Of course, any material used in preparing any dosage unit form should be pharmaceutically pure and substantially non-toxic in the amounts employed. In addition, the active compound(s) may be incorporated into sustained-release preparations and formulations.

The pharmaceutical composition may also comprise genetic molecules such as a vector capable of transfecting target cells where the vector carries a nucleic acid molecule encoding tumstatin or a modulatory agent as hereinbefore defined. The vector may, for example, be a viral vector.

The determination that reduced tumstatin levels in the airway tissue of individuals is linked to the airway tissue remodelling which occurs in the context of some airway diseases, such as asthma and LAM, has now provided a means of screening individuals to determine either whether any tissue remodelling which they are undergoing is linked to reduced tumstatin levels or whether those individuals who have not yet undergone airway tissue remodelling nevertheless exhibit a predisposition thereto. This is particularly important in the context of individuals who are newly diagnosed with disease conditions such as asthma or LAM but who have not yet undergone any tissue remodelling. By identifying whether such individuals may exhibit a predisposition to the onset of airway tissue remodelling provides an effective means for instituting prophylactic treatment regimens.

Accordingly, yet another aspect of the present invention is directed to a method for detecting susceptibility to the development of airway tissue remodelling in a mammal, said method comprising screening for the level of tumstatin protein and/or gene expression in said mammal or in an airway tissue derived biological sample from said mammal wherein a decrease in the level of tumstatin relative to the normal endogenous levels of a corresponding sample is indicative of the existence of said susceptibility.

Reference to "susceptibility" should be understood as a reference to both determining whether any existing remodelling events are linked to reduced tumstatin levels or whether individuals who have not yet undergone airway tissue remodelling nevertheless exhibit a predisposition thereto.

It should be understood that the biological sample which is screened in accordance with this aspect of the present invention may be any suitable sample which would be indicative of the tumstatin level of the airway tissue. The sample may be a biopsy sample of the airway tissue or it may be some other form of sample such as blood (serum), induced sputum, exhaled breath condensate, lavage samples.

Reference to "tumstatin", "airway tissue", "airway tissue remodelling", "mammal" and "normal endogenous level" should be understood to have the same meaning as hereinbefore defined.

Although the preferred method is to screen for a decrease in tumstatin levels in order to diagnose susceptibility to the occurrence of airway tissue remodelling, the detection of an increase in the level of this molecule may be desired under certain circumstances, for example, to monitor for improvement or responsiveness to a therapeutic or prophylactic treatment regimen. The present invention should therefore be understood to extend to screening for increases in tumstatin levels. The person of skill in the art would appreciate that in the context of this type of screening protocol one may seek to analyse a screening result relative to an earlier obtained result rather than only relative to normal levels.

Methods of screening for levels of tumstatin can be achieved by any suitable method which would be well known to persons of skill in the art. In this regard, it should be understood that reference to screening for the level of protein and/or gene expression "in a mammal" is intended as a reference to the use of any suitable technique which will provide information in relation to the level of expression of tumstatin in the relevant tissue of the mammal. These screening techniques include both in vivo screening techniques, as hereinafter described, as well as the in vitro techniques which are applied to a biological sample extracted from said mammal. Such in vitro techniques are likely to be preferred due to their significantly more simplistic and routine nature.

Since the present invention is predicated on screening for changes in the level of tumstatin such changes can in fact be screened for at the protein level or at the nucleic acid level, such as by screening for increases in the level of tumstatin mRNA transcripts. The person of skill in the art will determine the most appropriate means of analysis in any given situation. However it is generally preferred that screening be performed in the context of protein molecules due to the relative simplicity of the techniques which are likely to be utilised. Nevertheless in certain situations, and in the context of particular biological samples, it may be desirable or otherwise useful to directly analyse gene transcription.

Still further, to the extent that one is analysing a biological sample harvested from a patient, it is within the skill of the person in the art to determine the most appropriate sample for analysis.

As described above, means of screening for changes in levels of tumstatin in an individual, or biological sample derived therefrom, can be achieved by any suitable method, which would be well known to the person of skill in the art, such as but not limited to:

(i) In vivo detection of tumstatin. Molecular Imaging may be used following administration of imaging probes or reagents capable of disclosing altered expression levels of the tumstatin mRNA or protein expression product in the lung tissues.

Molecular imaging (Moore, A., Basilion, J., Chiocca, E., and Weissleder, R., BBA, 1402:239-249, 1988; Weissleder, R., Moore, A., Ph.D., Malumood-Bhorade, U., Benveniste, H., Chiocca, E. A., Basilion, J. P. *Nature Medicine,* 6:351-355, 2000) is the in vivo imaging of molecular expression that correlates with the macro-features currently visualized using "classical" diagnostic imaging techniques such as X-Ray, computed tomography (CT), MRI, Positron Emission Tomography (PET) or endoscopy.

(ii) Detection of up-regulation of mRNA expression in the tissue by Fluorescent In Situ Hybridization (FISH), or in extracts from the cells by technologies such as Quantitative Reverse Transcriptase Polymerase Chain Reaction (QRT-PCR) or Flow cytometric qualification of competitive RT-PCR products (Wedemeyer, N., Potter, T., Wetzlich, S, and Gohde, W. *Clinical Chemistry* 48:9 1398-1405, 2002) or array technologies.

For example, a labelled polynucleotide encoding tumstatin may be utilized as a probe in a Northern blot of an RNA extract obtained from a tissue. Preferably, a nucleic acid extract from the animal is utilized in concert with oligonucleotide primers corresponding to sense and antisense sequences of a polynucleotide encoding tumstatin, or flanking sequences thereof, in a nucleic acid amplification reaction such as RT PCR, real time PCR or SAGE. A variety of automated solid-phase detection techniques are also appropriate. For example, large scale immobilized primer arrays (VLSIPS™) are used for the detection of nucleic acids as, for example, described by Fodor et al., 1991 and Kazal et al., 1996. The above genetic techniques are well known to persons skilled in the art.

For example, to detect tumstatin encoding RNA transcripts, RNA is isolated from a cellular sample suspected of containing the tumstatin RNA. RNA can be isolated by methods known in the art, e.g. using TRIZOL™ reagent (GIBCO-BRL/Life Technologies, Gaithersburg, Md.). Oligo-dT, or random-sequence oligonucleotides, as well as sequence-specific oligonucleotides can be employed as a primer in a reverse transcriptase reaction to prepare first-strand cDNAs from the isolated RNA. Resultant first-strand cDNAs are then amplified with sequence-specific oligonucleotides in PCR reactions to yield an amplified product.

"Polymerase chain reaction" or "PCR" refers to a procedure or technique in which amounts of a preselected fragment of nucleic acid, RNA and/or DNA, are amplified as described in U.S. Pat. No. 4,683,195. Generally, sequence information from the ends of the region of interest or beyond is employed to design oligonucleotide primers. These primers will be identical or similar in sequence to opposite strands of the template to be amplified. PCR can be used to amplify specific RNA sequences and cDNA transcribed from total cellular RNA. See generally Mullis et al., 1987; Erlich, 1989. Thus, amplification of specific nucleic acid sequences by PCR relies upon oligonucleotides or "primers" having conserved nucleotide sequences. For example, one primer is prepared which is predicted to anneal to the antisense strand and another primer prepared which is predicted to anneal to the sense strand of a cDNA molecule which encodes the markers.

To detect the amplified product, the reaction mixture is typically subjected to agarose gel electrophoresis or other convenient separation technique and the relative presence of tumstatin specific amplified DNA detected. For example, the tumstatin amplified DNA may be detected using Southern hybridization with a specific oligonucleotide probe or comparing is electrophoretic mobility with DNA standards of known molecular weight. Isolation, purification and characterization of the amplified the markers DNA may be accomplished by excising or eluting the fragment from the gel (for example, see references Lawn et al., 1981; Goeddel et al., 1980), cloning the amplified product into a cloning site of a suitable vector, such as the pCRII vector (Invitrogen), sequencing the cloned insert and comparing the DNA sequence to the known sequence of the markers. The relative amounts of the markers mRNA and cDNA can then be determined.

(iii) Measurement of altered tumstatin levels in a suitable biological sample, either qualitatively or quantitatively, for example by immunoassay, utilising immunointeractive molecules such as monoclonal antibodies.

In one example, one may seek to detect the tumstatin-immunointeractive molecule complex formation. For example, an antibody according to the invention, having a reporter molecule associated therewith, may be utilized in immunoassays. Such immunoassays include but are not limited to radioimmunoassays (RIAs), enzyme-linked immunosorbent assays (ELISAs) and immunochromatographic techniques (ICTs), Western blotting which are well known to those of skill in the art. For example, reference may be made to "Current Protocols in Immunology", 1994 which discloses a variety of immunoassays which may be used in accordance with the present invention. Immunoassays may include competitive assays. It will be understood that the present invention encompasses qualitative and quantitative immunoassays.

Suitable immunoassay techniques are described, for example, in U.S. Pat. Nos. 4,016,043, 4,424,279 and 4,018,653. These include both single-site and two-site assays of the non-competitive types, as well as the traditional competitive binding assays. These assays also include direct binding of a labelled antigen-binding molecule to a target antigen. The antigen in this case is tumstatin or a fragment thereof.

Two-site assays are particularly favoured for use in the present invention. A number of variations of these assays exist, all of which are intended to be encompassed by the present invention. Briefly, in a typical forward assay, an unlabelled antigen-binding molecule such as an unlabelled antibody is immobilized on a solid substrate and the sample to be tested brought into contact with the bound molecule. After a suitable period of incubation, for a period of time sufficient to allow formation of an antibody-antigen complex, another antigen-binding molecule, suitably a second antibody specific to the antigen, labelled with a reporter molecule capable of producing a detectable signal is then added and incubated, allowing time sufficient for the formation of another complex of antibody-antigen-labelled antibody. Any unreacted material is washed away and the presence of the antigen is determined by observation of a signal produced by the reporter molecule. The results may be either qualitative, by simple observation of the visible signal, or may be quantitated by comparing with a control sample containing known amounts of antigen. Variations on the forward assay include a simultaneous assay, in which both sample and labelled antibody are added simultaneously to the bound antibody. These techniques are well known to those skilled in the art, including minor variations as will be readily apparent.

In the typical forward assay, a first antibody having specificity for the antigen or antigenic parts thereof is either covalently or passively bound to a solid surface. The solid surface is typically glass or a polymer, the most commonly used polymers being cellulose, polyacrylamide, nylon, polystyrene, polyvinyl chloride or polypropylene. The solid supports may be in the form of tubes, beads, discs of microplates, or any other surface suitable for conducting an immunoassay. The binding processes are well known in the art and generally consist of cross-linking covalently binding or physically adsorbing, the polymer-antibody complex is washed in preparation for the test sample. An aliquot of the sample to be tested is then added to the solid phase complex and incubated for a period of time sufficient and under suitable conditions to allow binding of any antigen present to the antibody. Following the incubation period, the antigen-antibody complex is washed and dried and incubated with a second antibody specific for a portion of the antigen. The second antibody has generally a reporter molecule associated therewith that is used to indicate the binding of the second antibody to the antigen. The amount of labelled antibody that binds, as determined by the associated reporter molecule, is proportional to the amount of antigen bound to the immobilized first antibody.

An alternative method involves immobilizing the antigen in the biological sample and then exposing the immobilized antigen to specific antibody that may or may not be labelled with a reporter molecule. Depending on the amount of target and the strength of the reporter molecule signal, a bound antigen may be detectable by direct labelling with the antibody. Alternatively, a second labelled antibody, specific to the first antibody is exposed to the target-first antibody complex to form a target-first antibody-second antibody tertiary complex. The complex is detected by the signal emitted by the reporter molecule.

From the foregoing, it will be appreciated that the reporter molecule associated with the antigen-binding molecule may include the following:—

(a) direct attachment of the reporter molecule to the antibody;
(b) indirect attachment of the reporter molecule to the antibody; i.e., attachment of the reporter molecule to another assay reagent which subsequently binds to the antibody; and
(c) attachment to a subsequent reaction product of the antibody.

The reporter molecule may be selected from a group including a chromogen, a catalyst, an enzyme, a fluorochrome, a chemiluminescent molecule, a paramagnetic ion, a lanthanide ion such as Europium ($Eu^{34}$), a radioisotope including other nuclear tags and a direct visual label.

In the case of a direct visual label, use may be made of a colloidal metallic or non-metallic particle, a dye particle, an enzyme or a substrate, an organic polymer, a latex particle, a liposome, or other vesicle containing a signal producing substance and the like.

A large number of enzymes suitable for use as reporter molecules is disclosed in U.S. Pat. No. 4,366,241, U.S. Pat. No. 4,843,000, and U.S. Pat. No. 4,849,338. Suitable enzymes useful in the present invention include alkaline phosphatase, horseradish peroxidase, luciferase, β-galactosidase, glucose oxidase, lysozyme, malate dehydrogenase and the like. The enzymes may be used alone or in combination with a second enzyme that is in solution.

Suitable fluorochromes include, but are not limited to, fluorescein isothiocyanate (FITC), tetramethylrhodamine isothiocyanate (TRITC), R-Phycoerythrin (RPE), and Texas Red. Other exemplary fluorochromes include those discussed by Dower et al., International Publication No. WO 93/06121. Reference also may be made to the fluorochromes described in U.S. Pat. Nos. 5,573,909 (Singer et al), 5,326,692 (Brinkley et al). Alternatively, reference may be made to the fluorochromes described in U.S. Pat. Nos. 5,227,487, 5,274,113, 5,405,975, 5,433,896, 5,442,045, 5,451,663, 5,453,517, 5,459,276, 5,516,864, 5,648,270 and 5,723,218.

In the case of an enzyme immunoassay, an enzyme is conjugated to the second antibody, generally by means of glutaraldehyde or periodate. As will be readily recognised, however, a wide variety of different conjugation techniques exist which are readily available to the skilled artisan. The substrates to be used with the specific enzymes are generally chosen for the production of, upon hydrolysis by the corresponding enzyme, a detectable colour change. Examples of suitable enzymes include those described supra. It is also possible to employ fluorogenic substrates, which yield a fluorescent product rather than the chromogenic substrates noted above. In all cases, the enzyme-labelled antibody is added to the first antibody-antigen complex, allowed to bind, and then the excess reagent washed away. A solution containing the appropriate substrate is then added to the complex of antibody-antigen-antibody. The substrate will react with the enzyme linked to the second antibody, giving a qualitative visual signal, which may be further quantitated, usually spectrophotometrically, to give an indication of the amount of antigen which was present in the sample.

Alternately, fluorescent compounds, such as fluorescein, rhodamine and the lanthanide, europium (EU), may be chemically coupled to antibodies without altering their binding capacity. When activated by illumination with light of a particular wavelength, the fluorochrome-labelled antibody adsorbs the light energy, inducing a state to excitability in the molecule, followed by emission of the light at a characteristic colour visually detectable with a light microscope. The fluorescent-labelled antibody is allowed to bind to the first antibody-antigen complex. After washing off the unbound reagent, the remaining tertiary complex is then exposed to light of an appropriate wavelength. The fluorescence observed indicates the presence of the antigen of interest. Immunofluorometric assays (IFMA) are well established in the art and are particularly useful for the present method. However, other reporter molecules, such as radioisotope, chemiluminescent or bioluminescent molecules may also be employed.

As detailed above, any suitable technique may be utilised to detect tumstatin or its encoding nucleic acid molecule. The nature of the technique which is selected for use will largely determine the type of biological sample which is required for analysis. Such determinations are well within the scope of the person of skill in the art. Typical samples which one may seek to analyse are biopsy samples of the airways.

The present invention also provides kits suitable for use in accordance with the methods of the invention. Such kits include for example diagnostic kits for assaying biological samples, comprising an agent for detecting tumstatin or encoding nucleic acid molecules and/or collagen IV α5 chain NC1 domain, and reagents useful for facilitating the detection by the agent(s). Further means may also be included, for example, to receive a biological sample. The agent(s) may be any suitable detecting molecule. Kits according to the present invention may also include other components required to conduct the methods of the present invention, such as buffers and/or diluents. The kits typically include containers for housing the various components and instructions for using the kit components in the methods of the present invention.

The present invention is further described by reference to the following non-limiting examples.

EXAMPLES

Example 1

Tissue Section Staining using Immunofluorescence

Lung tissue sections from a total of 15 asthmatics, 9 non-asthmatics and 10 volunteers with Lymphangioleiomyomatosis (LAM) were examined using immunohistochemistry. For 7 asthmatic patients, diagnosed according to the Global Initiative for Asthma (GINA) guidelines, bronchial biopsies were taken. In addition, biopsies were also taken from two volunteers who were shown not to have asthma according to GINA guidelines. For the remaining asthmatic and non-asthmatic individuals tissue was sourced from a tissue bank. In the case of asthmatic samples, many of these were derived from individuals who had died of asthma (status asthmaticus). Diagnosis of LAM was made by respiratory physician with the aid of a CT scan.

The presence of the non-collagenous 1 (NC1) domain of the collagen IV α3 chain (tumstatin) was examined in all tissue sections. The presence of the non-collagenous 1 (NC1) domain of the collagen IV α1,2,3,4,5 and 6 chains in comparison to the staining observed using isotype control antibodies was examined in 5 asthmatics, 4 non-asthmatics, and 8 patients with LAM. Isotype control antibodies (an antibody of the same species which is not raised against human antigens) confirm that the collagen IV α1-6 NC1 antibody staining is not non-specific. The primary antibodies (collagen IV α1-6 NC1) and the isotype control antibodies were detected using a secondary antibody directly conjugated to Fluorescein isothiocyanate (FITC), and the resulting image was viewed using a fluorescence microscope. The lung tissue samples were either bronchial rings (dissected from lung, formalin fixed and embedded in paraffin wax) or fresh frozen biopsies obtained by bronchoscopic biopsy of the right middle lobe. It is likely that these tissue samples contain the following cell types: epithelial cells, fibroblasts, smooth muscle cells, endothelial cells and inflammatory cells (macrophages, T cells, mast cells, and eosinophils) all of which could be potential targets for the actions of tumstatin.

Example 1A

Paraffin embedded tissue sections of bronchial rings from 8 asthmatics, 7 non-asthmatics and 10 LAM patients were deparaffinised and rehydrated through graded alcohol. Blocking serum was then added to the sections (10% non-immune horse serum) for 20 minutes at room temperature. Without rinsing, either primary antibodies (collagen IV α1-6 NC1 Shigei Medical Research Institute, Okayama, Japan [1 ng/ml]) or isotype control antibodies (Goat IgG, Jackson ImmunoResearch PA, USA [1 ng/ml]) were added to the sections and incubated for 1 hour at room temperature. Sections were then washed with phosphate buffered saline (PBS) and a rat anti-goat FITC-conjugated secondary antibody (MP Biomedicals Ohio, USA [1 ng/ml]) was added, and incubated for 30 minutes at room temperature. Sections were then rinsed with PBS (to wash away unbound secondary antibody) and mounted using vestashield mounting media (Vecta Laboratories USA). Images were taken on an Olympus fluorescence microscope and captured using Leica imaging software.

In addition, sections from fresh frozen biopsies from 6 volunteers with asthma and 2 non-asthmatics were also stained as above, minus the deparaffinising step in order to ensure that the process of embedding in paraffin wax did not affect the staining procedure used.

Figure 2:
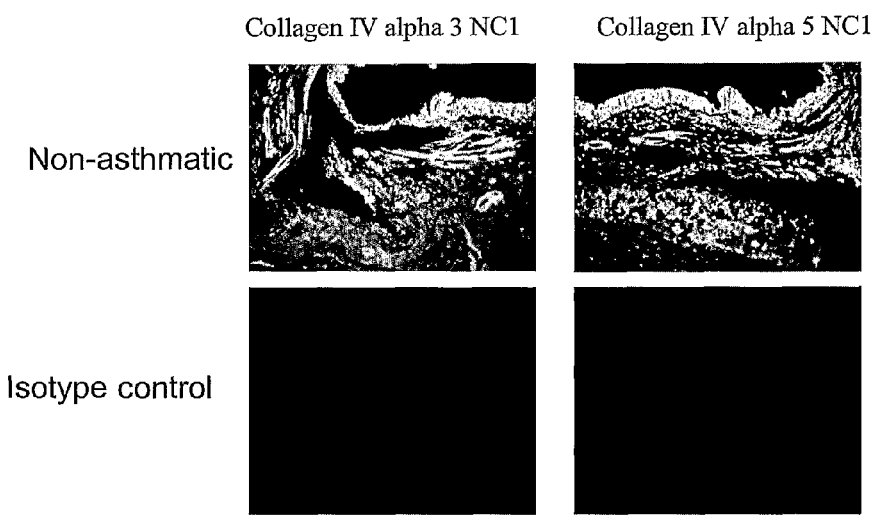
FIG. 2. Images depicting positive staining for collagen IV α3 and α5 chain NC1 domains in sections of bronchial rings derived from a non-asthmatic patient in comparison to staining observed using the appropriate isotype control. These immunohistochemical images are representative of all non-asthmatic patients tested (n=9).
Figure 3:
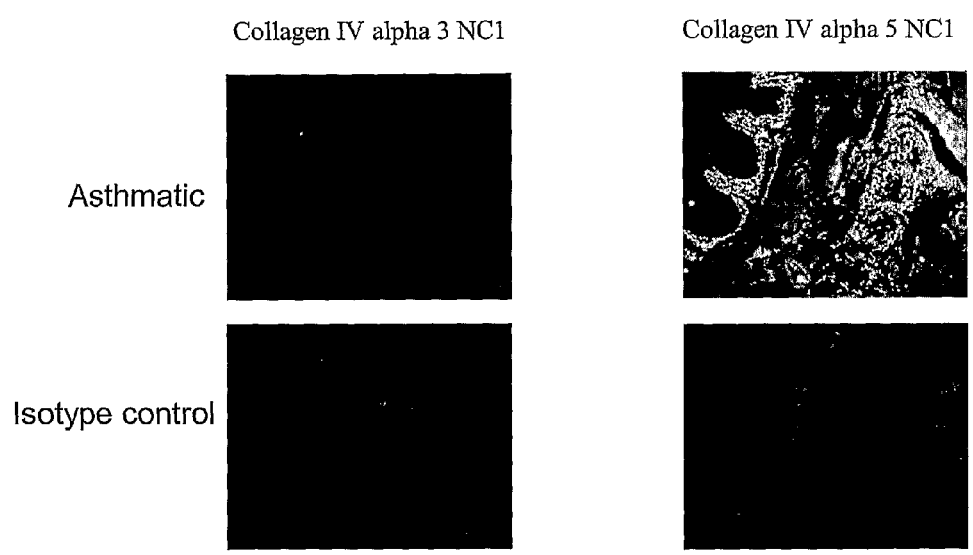
FIG. 3. Images depicting the absence of collagen IV α3 chain NC1 domain in sections of bronchial rings derived from an asthmatic patient in comparison to staining observed using the appropriate isotype control. There is positive staining for collagen IV α5 chain NC1 domain in sections derived from the same asthmatic subject. These immunohistochemical images are representative of all asthmatic subjects tested (n=14).

Collagen IV α3 (NC1 Domain) and Collagen IV α5 (NC1 Domain) in Asthmatic and Non-Asthmatic Bronchial Ring Tissue Sections As shown in FIG. 1, in the bronchial ring tissue sections from asthmatic subjects staining for collagen IV, α3 (NC1 domain) was absent and this was observed in all 8 asthmatic patients studied. In comparison and also shown in FIG. 1, in the bronchial ring tissue sections from 2 non-asthmatic subjects there was positive staining for the NC1 domain of the α3 chain of collagen IV, and this was observed in all 7 non-asthmatic subjects studied. The presence of the NC1 domains of collagen IV α 1,2,4,5 and 6 was confirmed by positive staining in all asthmatic bronchial ring tissue sections, and all NC1 domains of the six α chains of collagen IV were present in all non-asthmatic bronchial ring tissue sections examined (FIG. 1). As shown in greater detail in FIG. 2, positive staining for collagen IV α3 (NC1 domain) and α5 (NC1 domain) chains was observed in sections of bronchial rings derived from a non-asthmatic patient in comparison to the staining observed using isotype control antibodies. Similarly, FIG. 3 demonstrates the absence of the collagen IV α3 (NC1 domain) chain, and the presence of the collagen IV α5 (NC1 domain) chain in sections of bronchial rings derived from an asthmatic patient in comparison to staining observed using the appropriate isotype control. This demonstrates that the staining technique used is capable of detecting the NC1 domains of the α3 and α5 chains of collagen IV if present in the tissue sample.

Figure 4:
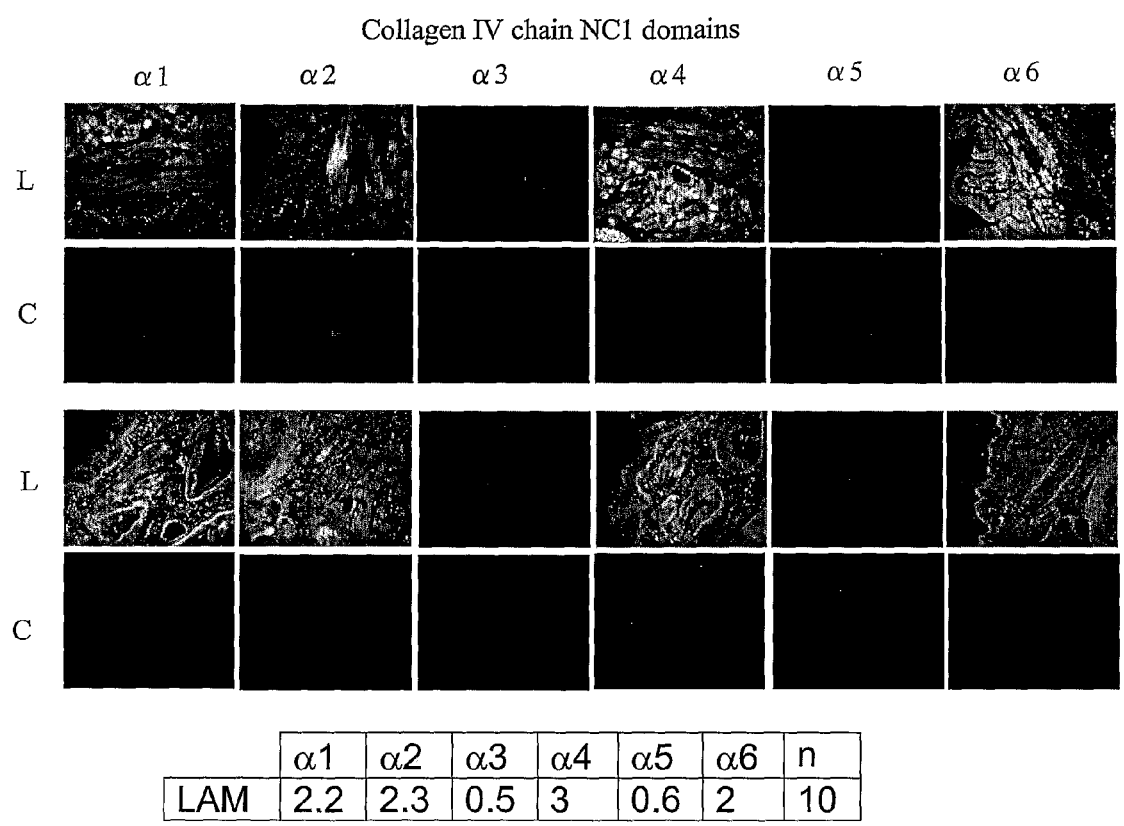
FIG. 4. Images depicting staining for the NC1 domains of collagen IV α 1,2,4 and 6 chains in sections of bronchial rings derived from 2 subjects who have lymphangioleiomyomatosis (LAM). These immunohistochemical images are representative of results from 8 subjects with lymphangioleiomyomatosis.

Collagen IV α3 (NC1 Domain) and Collagen IV α5 (NC1 Domain) in Bronchial Ring Tissue Sections Derived from Subjects with LAM As shown in FIG. 4, staining for both collagen IV α3 (NC1 domain) and collagen IV α5 (NC1 domain) was absent in tissue sections derived from LAM patients, in comparison to the isotype control staining. In contrast, and also shown in FIG. 4, positive staining for collagen IV α chains 1,2,4 and 6 (NC1 domains) in sections was observed in the bronchial ring tissue sections derived from subjects with LAM. These findings were observed in 8 LAM patients studied.

Collagen IV α3 (NC1 Domain) and Collagen IV α5 (NC1 Domain) in Asthmatic and Non-Asthmatic Bronchial Biopsy Tissue Sections.

Figure 5:
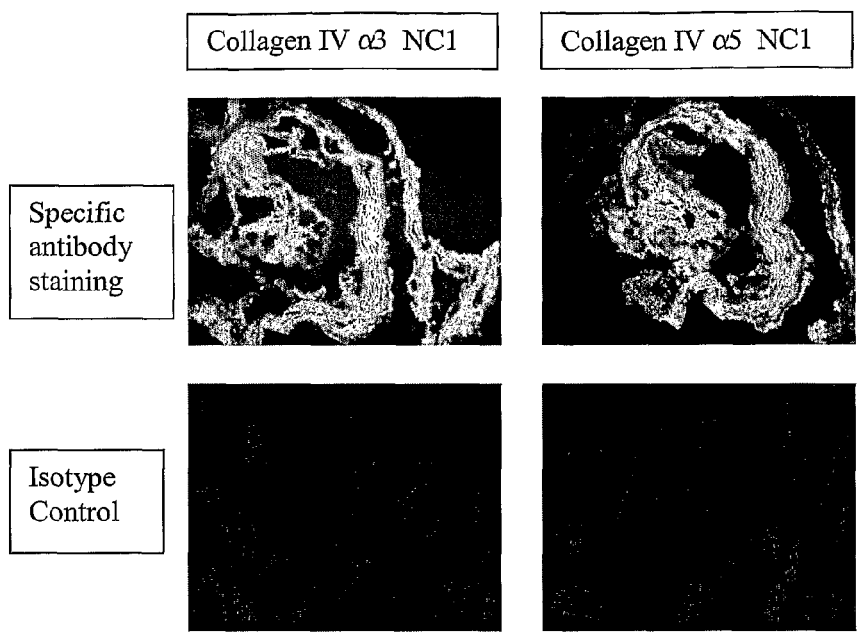
FIG. 5. Images depicting positive staining for collagen IV α3 and α5 chain NC1 domains in sections of a bronchial biopsy derived from a non-asthmatic patient, in comparison to staining observed using the appropriate isotype control. These immunohistochemical images are representative of all non-asthmatic patients tested (n=9).
Figure 6:
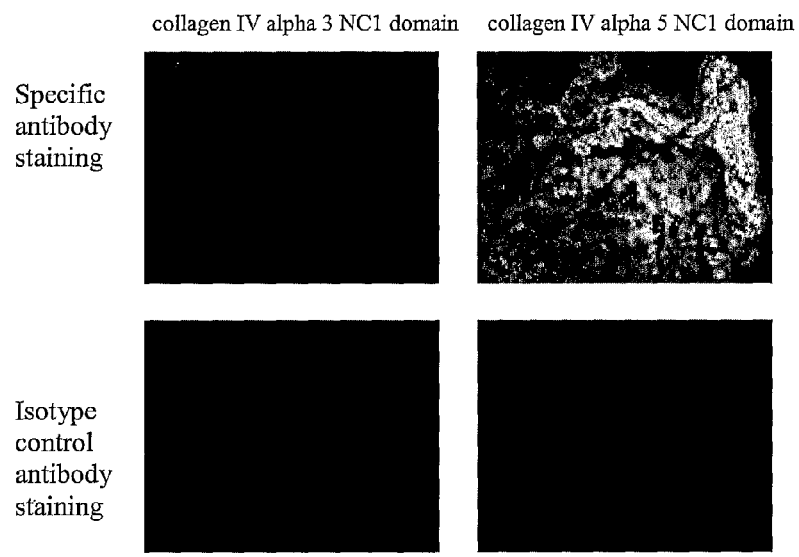
FIG. 6. Images depicting the absence of collagen IV α3 chain NC1 domain in sections of a bronchial biopsy derived from an asthmatic patient, in comparison to staining observed using the appropriate isotype control. There is positive staining for collagen IV α5 chain NC1 domain in sections derived from the asthmatic subject. These immunohistochemical images are representative of all tested (n=15).

To confirm that the absence of collagen IV α3 (NC1 domain) observed in bronchial ring tissue sections from asthmatic subjects was not due to an artefact of the tissue preparation process, fresh frozen bronchial biopsies obtained from the right middle lobe from six volunteers with asthma and 2 volunteers without asthma were immunohistochemically examined. As shown in FIG. 5, positive staining for the collagen IV α3 and α5 chains (NC1 domains) was observed in bronchial biopsy sections derived from a non-asthmatic volunteer, in comparison to staining observed using the appropriate isotype control. The absence of the collagen IV α3 chain (NC1 domain), in comparison to staining observed using the appropriate isotype control, in sections of a bronchial biopsy derived from asthmatic volunteers is demonstrated in FIG. 6. There is positive staining for the collagen IV α5 chain (NC1 domain) in fresh frozen bronchial biopsy sections derived from asthmatic subjects. These findings were observed in sections from bronchial biopsies in all six asthmatic subjects tested.

Semi-Quantitative Analysis for the Presence of Collagen IV α3 and α5 Chains (NC1 Domains)

As shown in Table 2, images from all patients were scored by three independent observers, who were blinded to the diagnosis of the subject, for the presence and intensity of staining. Images were scored as follows: 0=absence of stain; 1=thin and discontinuous staining; 2=thin and continuous detection; 3=strong and continuous staining.

TABLE 2

The average scores of immunohistochemical staining obtained by 3 independent observers for all tissue sections (asthma n = 14, non-asthma n = 7 and LAM n = 10)

|  | Collagen IV α3 NC1 | Collagen IV α5 NC1 |
|---|---|---|
| Asthmatic | 0 | 2.16 |
| Non-asthmatic | 2.29 | 2.47 |
| LAM | 0.5 | 0.56 |

Example 1B

Colorimetric Analysis of Stained Tissue Sections

To further validate the above findings (Example 1A) and further investigate the pattern of tissue expression of collagen IV α3, it was investigated whether the 7 s domain of collagen IV α3 was present in tissue sections from asthmatic and non-asthmatic fresh frozen bronchial biopsies as well as paraffin sections from LAM and non-asthmatic patients. In addition it was investigated whether the NC1 domain of collagen IV α3 was present in a further asthmatic volunteer. In contrast to the staining protocol described in Example 1A, the inventors here used an automated quantitative colorimetric analysis of the staining patterns.

Figure 7:
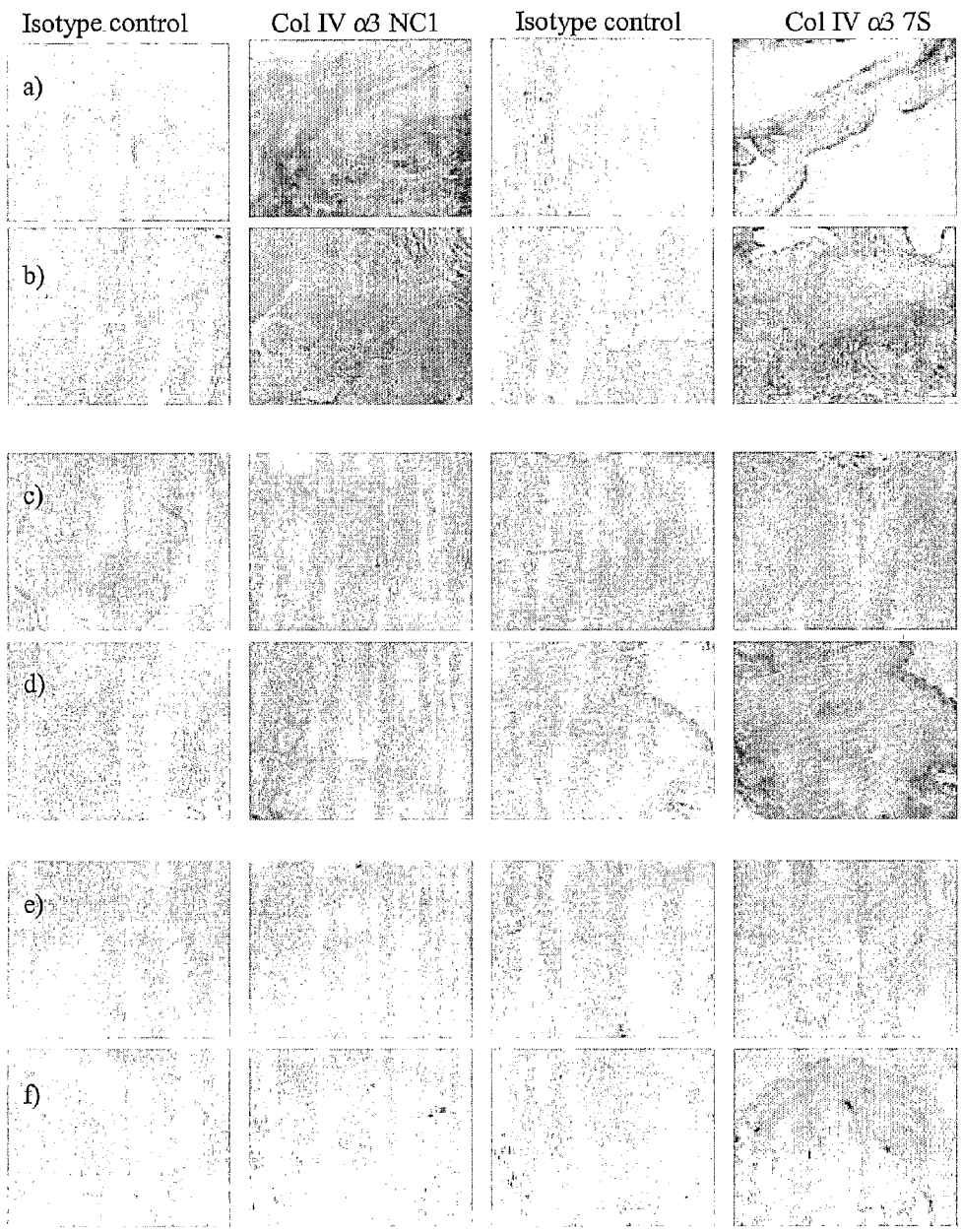
FIG. 7. Images depicting positive staining for collagen IV α3 NC1 domain in tissue sections derived from two non-asthmatic volunteers (a and b) and is representative of all five tested. In contrast no specific staining was observed in the two volunteers with LAM (c and d) or the two volunteers with asthma (e and f). However the 7 s domain of collagen IV α3 was present in the tissue sections obtained from the non-asthmatic volunteers and the volunteers with LAM and asthma. Each row contains images derived from tissue sections obtained from the same volunteer and are representative of all tested (non-asthmatic n=5, LAM n=5 and asthmatic n=5).

Frozen sections were thawed and placed into PBS buffer for 5 minutes. Paraffin sections were de-paraffinised and placed in water for 5 minutes. Sections were blocked using a pre-made peroxidase block (DakoCytomation, Denmark) for 5 minutes. Primary antibodies were then added, Mouse anti-human collagen IV α3 NC1 (Weislab, Sweden) at a 1:50 dilution, chicken anti-human collagen IV α7 s (GenWay Biotech, Inc. CA USA) at a 1:100 dilution or isotype control antibodies (Mouse IgG, (R&D Systems) or Chicken IgY (Abcam, Cambridge, UK respectively), and incubated for 1 hour at room temperature. Sections were rinsed with buffer and a secondary peroxidase labelled antibody was added, a pre-made anti-mouse HRP (Dakocytamation, Denmark) was added against the NC1 primary antibody, rabbit anti-chicken HRP labelled antibody (Abcam, Cambridge, UK) was added against the 7 s antibody (1 μg/ml), and incubated for 1 hour at room temperature. Sections were washed in buffer for 5 minutes and a pre-made substrate chromogen solution (Liquid DAB+) (DakoCytomation, Denmark) was then added for 5 minutes. Sections were rinsed with distilled water and mounted using an aqueous mounting medium (Faramount aqueous mounting medium, DakoCytomation, Denmark) and coverslipped. When isotype controls were used, primary antibody was substituted with, Mouse $IgG_1$ (R&D Systems) and Chicken IgY (Abcam, Cambridge, UK). Images were taken on an Olympus microscope and captured and analysed using Leica imaging software. Consistent with the findings described in Example 1A, the NC1 domain of collagen IV α3 chain was absent in a further 6 asthmatic volunteers and in different tissue sections from 5 of the same volunteers with LAM using an automated image analysis program. Further, also consistent with Example 1A, the NC1 domain of collagen IV α3 chain was present in control tissue sections (2=frozen, 3=paraffin). However as shown in FIG. 7, the 7 s domain of the collagen IV α3 chain was present in tissue sections from asthmatic, LAM and control sections. This implies that cells within the airways of asthmatics and LAM patients are capable of producing collagen IV α3, however the NC1 domain is either cleaved or not produced at the protein level.

Figure 8:
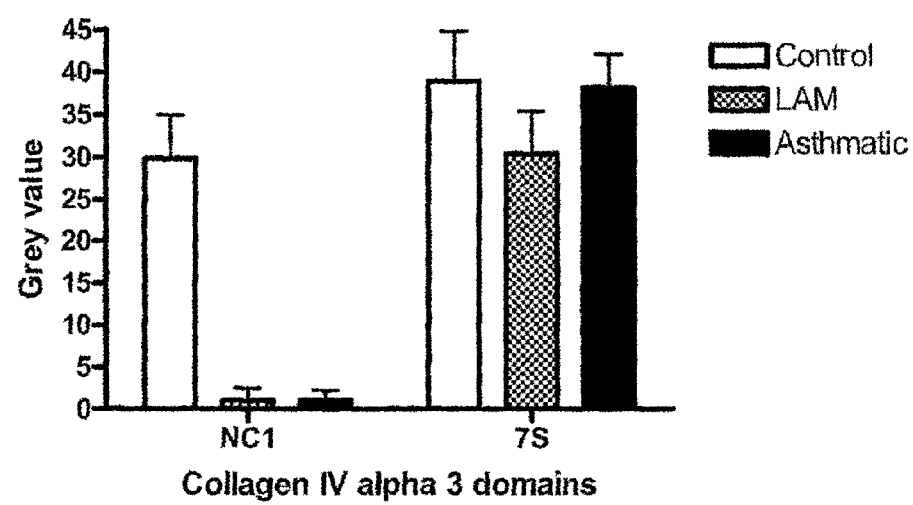
FIG. 8. Graphical representation of the computerised analysis of the specific staining for the NC1 and 7 s domains of the collagen IV α3 molecule. The Y axis represents the grey scale value obtained when the specific staining value is normalised to the respective isotype control level. Significantly lower amounts of the NC1 domain were present in tissue sections from both asthmatic (n=6) and LAM (n=5) in comparison to the non-asthmatic volunteers (n=5) (for both $p<0.01$, ANOVA with Dunnett's Multiple Comparison Test). However no difference was observed in the expression of the 7 s domain of collagen IV α3 between tissues sections derived from LAM or asthmatic volunteers in comparison to the non-asthmatic volunteers.

The expression of both the NC1 domain and the 7 s domain of the collagen IV α3 chain were quantified using gray scale image analysis. A single image, from each patient, which contained an airway and parenchyma was used. From this 10 random areas were selected for gray scale analysis. The data presented in FIG. 8 were obtained by subtracting the corresponding gray scale values obtained from the isotype control staining from the values obtained from the specific antibody staining. The expression of the 7 s domain did not significantly differ between the tissue sections examined.

The results described above indicate a significant down-regulation of expression, at the protein level, of the NC1 domain of collagen IV α3 chain (hereinafter "tumstatin") in asthmatic and LAM patients.

Example 2

Polymerase Chain Reaction to Determine the Presence of Tumstatin mRNA

To evaluate whether or not mRNA encoding tumstatin is present in asthmatic airway cells the expression of tumstatin specific mRNA was measured using real time PCR. As a control the expression of mRNA encoding collagen IV α1 and α5 in the same samples was also measured.

Airway smooth muscle cells (isolated from non-asthmatic, asthmatic and LAM individuals) and fibroblasts from non-asthmatic individuals were isolated and seeded into 75 $cm^2$ tissue culture flasks at a density of $1 \times 10^4$ cells/$cm^2$ in DMEM containing 5% FBS and 1% antibiotics. Endothelial cells from non-asthmatic individuals were seeded as above in F-12 (HAMS nutrient F-12, JRH Biosciences) containing endothelial cell growth supplement (ECG, BD Biosciences, MA USA) and 10% fetal bovine serum (FBS) (GIBCO, Invitrogen corporation. Batch: 1236374). All cell types were grown for 9 days at 37° C./5% $CO_2$, at which point they were lysed using lysis buffer provided in the NucleoSpin RNA II kit (Macherey-Nagel GmbH & Co, Duren Germany) and stored at −20° C. prior to extraction.

Total cellular RNA was extracted using the NucleoSpin RNA II kit according to the manufacturer's instructions. After extraction, samples were eluted in 40 μl RNase free water and stored at −20° C. until use. RNA was converted into cDNA using M-MLV Reverse Transcriptase (Invitrogen, CA, USA) with Recombinant Ribonuclease Inhibitor (Invitrogen, CA, USA) and the dNTP set (Invitrogen, CA, USA) in the presence of Random Primers (New England Biolabs, MA, USA), according to the manufacturer's instructions.

Real time quantitative PCR was performed in the ABI Prism 7000 Sequence Detection System (Applied Biosystems, Melbourne, Aus). The thermal cycle conditions consisted of 40 cycles of 95° C. for 15 seconds and 60° C. for 1 minute. Data files were generated using 7000 System Software, v1.2.3 (Applied Biosystems, Melbourne, Australia). All evaluation by PCR was carried out in triplicate, and normalised to the expression of the housekeeping gene 18S rRNA.

Figure 9:
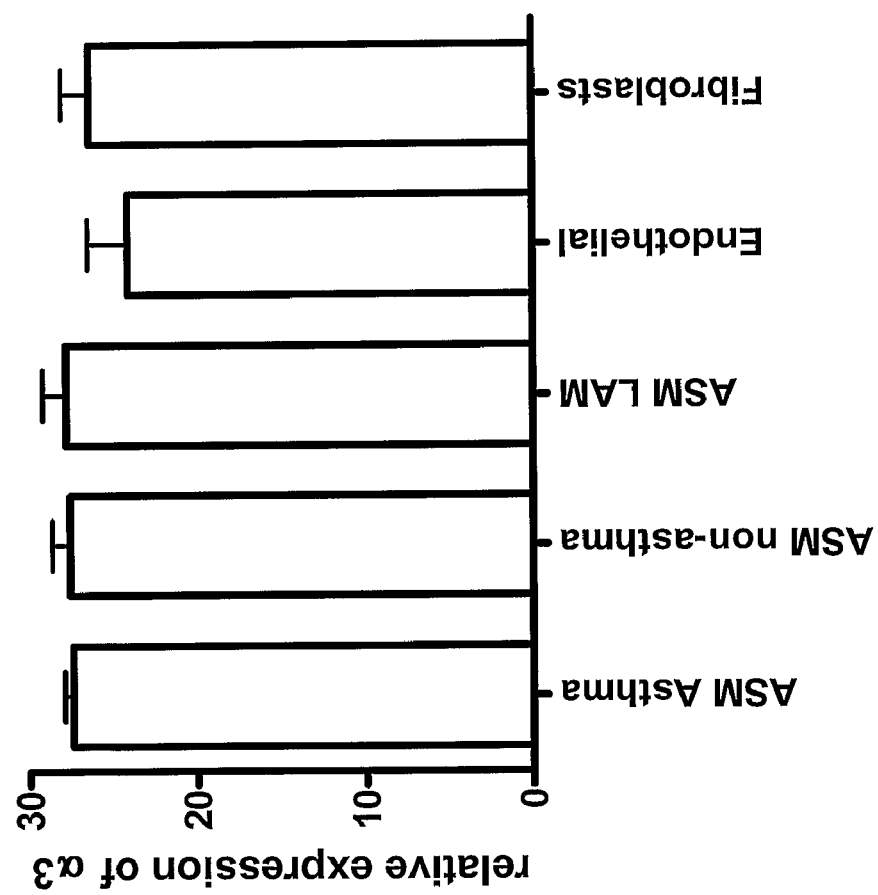
FIG. 9. The expression of mRNA encoding tumstatin normalised to the expression of the housekeeping 18S rRNA gene was measured using real time quantitative PCR. Tumstatin mRNA was found to be present in ASM cells isolated from volunteers with asthma (n=4), non-asthma (n=3), LAM (n=3), and COPD (n=3). In addition endothelial cells (n=4) and fibroblasts (n=3) from non-asthmatics were also found to express mRNA encoding for tumstain.
Figure 10:
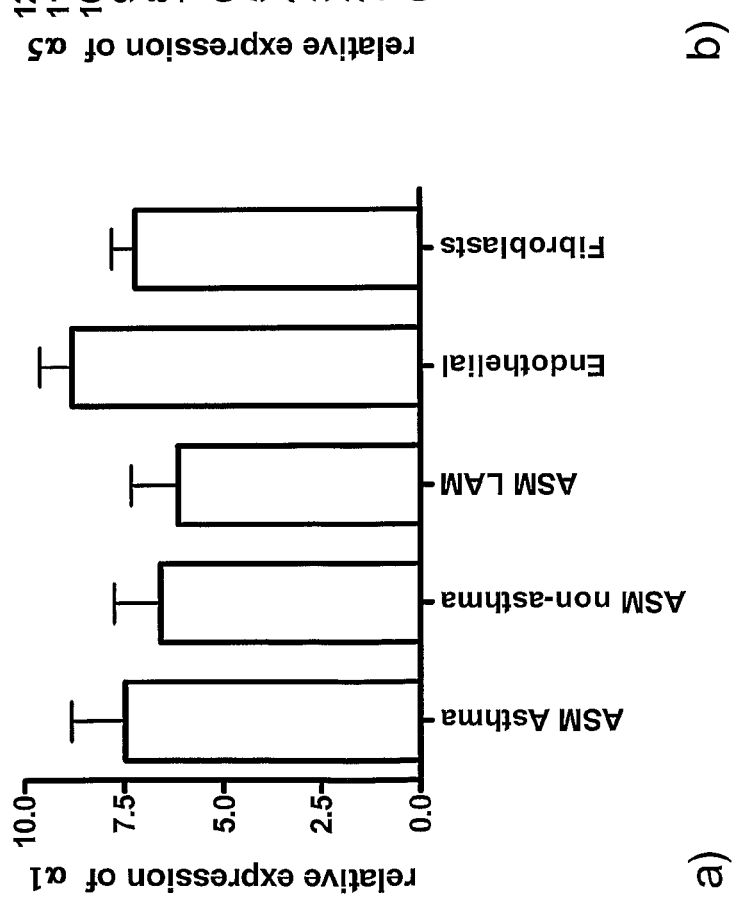
FIG. 10. The expression of mRNA encoding the α1 (a) and α5 (b) chains of collagen IV normalised to the expression of the housekeeping 18S rRNA gene was measured using real time quantitative PCR. Collagen IV α1 mRNA was found to be present in ASM cells isolated from volunteers with asthma (n=3), non-asthma (n=4), LAM (n=3), and COPD (n=3). In addition endothelial cells (n=5) and fibroblasts (n=3) from non-asthmatics were also found to express mRNA encoding for collagen IV α1. The collagen IV α5 mRNA was found to be present in ASM cells isolated from volunteers with asthma (n=3), non-asthma (n=4), LAM (n=3), and COPD (n=3). In addition endothelial cells (n=4) and fibroblasts (n=3) from non-asthmatics were also found to express mRNA encoding for collagen IV α5.
Figure 10:
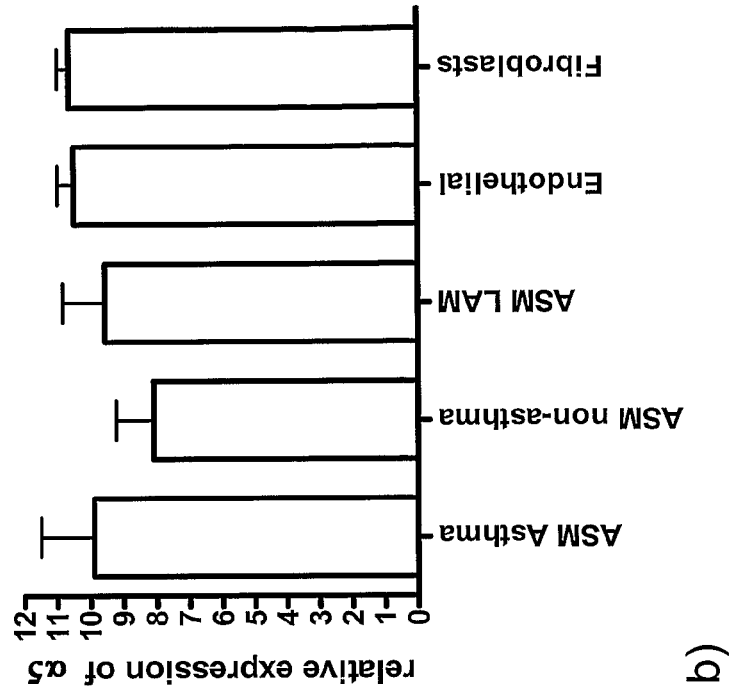

Briefly, each sample was analysed in triplicate in 25 μl reactions containing Universal PCR Master Mix, No AmpErase UNG Reagents Kit (Applied Biosystems, Melbourne, Australia) and the assay on demand primers Hs00266237_ml (α1), Hs 01022542_ml (tumstatin (α3)) or Hs00166712_ml (collagen IV α5) (all from Applied Biosystems). Each reaction was multiplexed with primers for 18S rRNA (Applied Biosystems, Melbourne, Aus) and 1 μl of cDNA/replicate was used for tumstatin, and 8 μl of cDNA/replicate was used for both collagen IV α1 and α5.

mRNA encoding tumstatin was found to be present in airway smooth muscle cells isolated from asthmatic, non-asthmatic and LAM volunteers and in fibroblasts and endothelial cells from non-asthmatics (FIG. 9). No statistical difference in the expression of tumstatin was observed in the cells examined (>0.05, one way ANOVA). Similarly mRNA encoding the α1 and α5 chains of collagen IV was found to be expressed in all cell types tested (FIG. 10), and no statistical difference in the expression was observed between the various cell types p>0.05, one way ANOVA).

These findings indicate that the absence of tumstatin protein in the airway tissue sections derived from both asthmatics and LAM sufferers, and the NC1 domain of the α5 chain of the collagen IV protein molecule in the airway tissue sections derived from LAM sufferers (as described in Example 1) is not the direct result of the inability of the airway cells to produce the appropriate mRNA. Rather the absence of these proteins appears to be due to a post-transcriptional event.

Example 3

Tumstatin Inhibits the Proliferation of Primary Lung Endothelial Cells but not other Mesenchymal Cells Airway smooth muscle (ASM) cells were isolated from lung tissue from volunteers with asthma or LAM and those without asthma (non-asthmatic). Primary pulmonary fibroblasts and primary pulmonary endothelial cells were isolated from non-asthmatic volunteers. The potential ability of tumstatin to inhibit the proliferation of these cell types was assessed.

Cell Isolation

Human airway smooth muscle cells were isolated by microdissection from bronchial tissue obtained from either bronchoscopy, lung tissue obtained from lung transplants, or lung tissue resected at thoracotomy. Ethical approval for the use of the lung tissue for/in vitro/experimentation was granted by the Human Ethics Committee of the University of Sydney, and the Sydney South West Area Health Service, and informed consent was received from all subjects. Asthmatic ASM cells were isolated from airway biopsies, and all but one of the non asthmatic derived ASM cells were isolated from either resected lung tissue, or lung transplantation (both donor and recipient)

This isolation and culture of ASM cells was carried out according to a method described by Johnson et al. 1995. Briefly, with the use of a dissecting microscope, sterile equipment and aseptic technique, bronchial airways were dissected from the surrounding parenchyma and cut longitudinally. The bronchi were then briefly dipped in 70% (v/v) ethanol in water to kill any surface organisms. The bronchi were then washed in sterile Hanks balanced salt solution three times and pinned down in a sterile Petri dish with the epithelial surface facing upwards. Using a dissecting microscope, the epithelium was removed with fine forceps in order to expose the smooth muscle bundles. The smooth muscle bundles were dissected free from the surrounding tissue and placed in a sterile 15 ml Falcon tube containing Hanks. The Falcon tube was then centrifuged at 200 g for 5 minutes. Isolated pieces of muscle were placed into 25 $cm^2$ vented tissue culture flasks (Falcon Labware) containing 2.5 mls of 10% FBS in Dulbecco's modified Eagle's medium (DMEM) supplemented with 20 U/ml penicillin, 20 g/ml streptomycin, and 2.5 g/ml amphotericin B. Flasks were then placed in a humidified $CO_2$ incubator (5% $CO_2$ in air) and maintained at 37° C.

Human airway epithelial cells were obtained from bronchi obtained from tissue removed during transplantation or resection. Bronchial airways were dissected from the surrounding parenchyma and cut longitudinally. The bronchi were then briefly dipped in 70% (v/v) ethanol in water to kill any surface organisms. The bronchi were then washed in sterile Hanks balanced salt solution three times and pinned down in a sterile petri dish with the epithelial surface facing upwards. Using a dissecting microscope, the epithelium was removed and placed in a sterile 15 ml Falcon tube containing Hanks. The Falcon tube was then centrifuged at 200 g for 5 minutes. Isolated pieces of epithelium were placed in a 25 $cm^2$ vented tissue culture flasks (Falcon Labware) containing 2.5 mls Basal Epithelial Growth medium (BEGM, Clonetics, USA), containing BPE 2 ml, insulin 0.5 ml, HC 0.5 ml, GA-1000 0.5 ml, retinoic acid 0.5 ml, transferrin 0.5 ml, triiodothyronine 0.5 ml, epinephrine 0.5 ml, and hEGF 0.5 ml (Cambrex Bio science, MD, USA). Flasks were then placed in a humidified $CO_2$ incubator (5% $CO_2$ in air) and maintained at 37° C.

Human pulmonary endothelial cells were isolated from bronchial tissue obtained during lung transplantation. Blood vessels were dissected free from surrounding tissue and cut longitudinally and then cut into approximately 5 mm segments. Blood vessel segments were then placed in a 15 ml falcon tube containing 10 ml of digestive buffer, (1 mg (250 U)/ml type 2 collagenase, 1 U/ml dispase, 10 mg/ml BSA) the tube was placed in the incubator for 10 minutes and agitated every 2 minutes. Digestive mixture was changed every 10 minutes for a total of 50 minutes. 1/10 volume of FBS was added to the supernatants that were removed every 10 minutes. Supernatants were then centrifuged at 200 g for 5 minutes. Supernantants were removed and cells were washed with culture medium, this contained 10% FBS, 10 µg/ml endothelial cell growth supplement, 20 U/ml heparin and 2% antibiotics, and centrifuged at 200 g for 5 minutes. Supernantants were removed and cells were placed in 75 $cm^2$ vented tissue culture flasks (Falcon Labware) containing 10 ml of culture medium, and incubated for 1 hour at 37° C. Unattached cells were centrifuged at 200 g for 5 minutes and placed in new 75 $cm^2$ vented tissue culture flasks (Falcon Labware) containing 10 ml of culture medium, (Flask was pre-coated with 0.2% (w/v) gelatin). Flasks were then placed in a humidified $CO_2$ incubator (5% $CO_2$ in air) and maintained at 37° C.

For fibroblast isolation, subpleural parenchyma was diced into 2 $mm^3$ pieces and approximately 5-7 pieces were seeded onto pre-wetted 25 $cm^2$ cell culture flasks. Flasks were maintained in Dulbecco's modified Eagle's medium (DMEM) (Invitrogen, Heidelberg, Australia) supplemented with 10% fetal bovine serum (FBS), 100 U/ml penicillin, 100 µg/ml streptomycin and amphotericin. Flasks were then placed in a humidified $CO_2$ incubator (5% $CO_2$ in air) and maintained at 37° C.

Endothelial cells were grown in F-12 (HAMS Nutrient F-12, JRH Biosciences) with endothelial cell growth supplement (ECG, BD Biosciences, MA USA) containing 10% FBS (GIBCO, Invitrogen corporation. Batch: 1236374). F12 containing 0.1% insulin transferrin and selenium (ITS, GIBCO, Invitrogen corporation, Auckland, NZ) for 24 hours was used to quiesce the cells. All remaining cell types thus isolated were grown in 96 well plates at an initial density of $1 \times 10^4$ cells/$cm^2$ in Dulbecco's modified eagle's medium (DMEM, SAFC Biosciences, Kansas, USA) containing 5% FBS (GIBCO, Invitrogen corporation. Batch: 1236374) (growth medium) for a period of 24 hours. The cells were then washed three times using Hanks buffer salt solution and placed in DMEM containing 0.1% insulin transferrin and selenium (ITS, GIBCO, Invitrogen corporation, Auckland, NZ) for 24 hours to quiesce the cells. Following washing as before, growth medium was added to the cells.

The synthetic tumstatin derived peptides T3 (Leu-Gln-Arg-Phe-Thr-Thr-Met-Pro-Phe-Leu-Phe-Cys-Asn-Val-Asn-Asp-Val-Cys-Asn-Phe; SEQ ID NO:6) dissolved in water or T7 (Thr-Met-Pro-Phe-Leu-Phe-Cys-Asn-Val-Asn-Asp-Val-Cys-Asn-Phe-Ala-Ser-Arg-Asn-Asp-Tyr-Ser-Tyr-Trp-Leu; SEQ ID NO:7) dissolved in 4% Acetonitrile (Phoenix pharmaceuticals, CA USA) were added at 4.5 µM to some of the cells. 4% Acetonitrile was used alone as a vehicle control. These peptides were replaced after the initial 24 hours and then after every 48 hours. Proliferation was assessed using an MTT assay (SIGMA-aldrich, Missouri, USA) at day 3, 7 and 9. Briefly 100 µl of MTT was added to each well for 5 hours at 37° C. followed by the addition of 100 µl of filtered 10% SDS in 0.01 M HCl overnight. The specific absorption of each well was measured at 690 nm (reference) and 570 nm.

Figure 11:
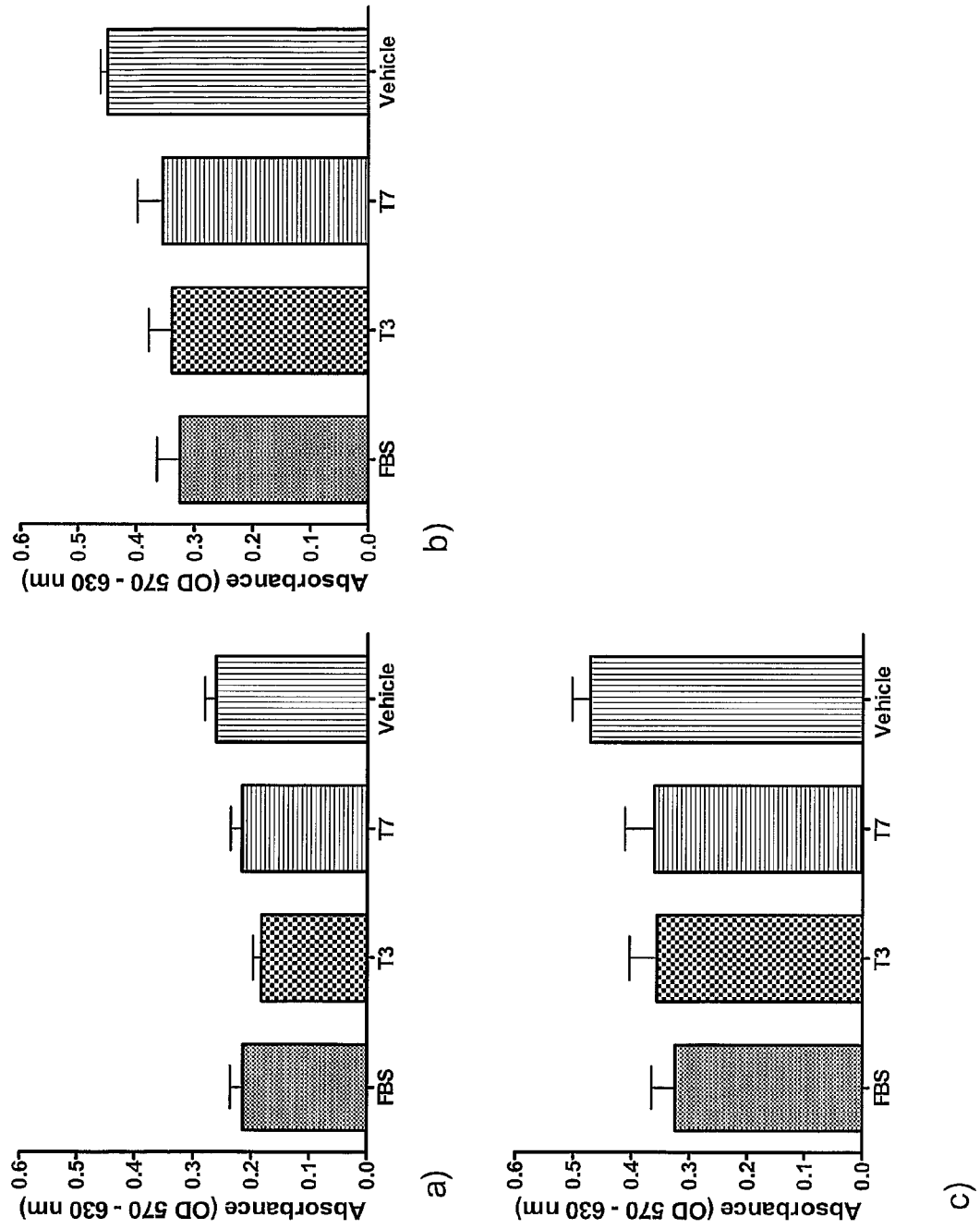
FIG. 11. The proliferation of asthmatic smooth muscle cells induced by FBS was not inhibited by the addition of T3 or T7 tumstatin derived peptides at a) 1 day, b) 3 days or c) 9 days. n=4 ASM cell lines derived from 4 independent volunteers. Bars indicate means +/− standard error of the mean. The vertical axis denotes the specific formation of formazan in the mitochondria indicating the total number of live cells.
Figure 12:
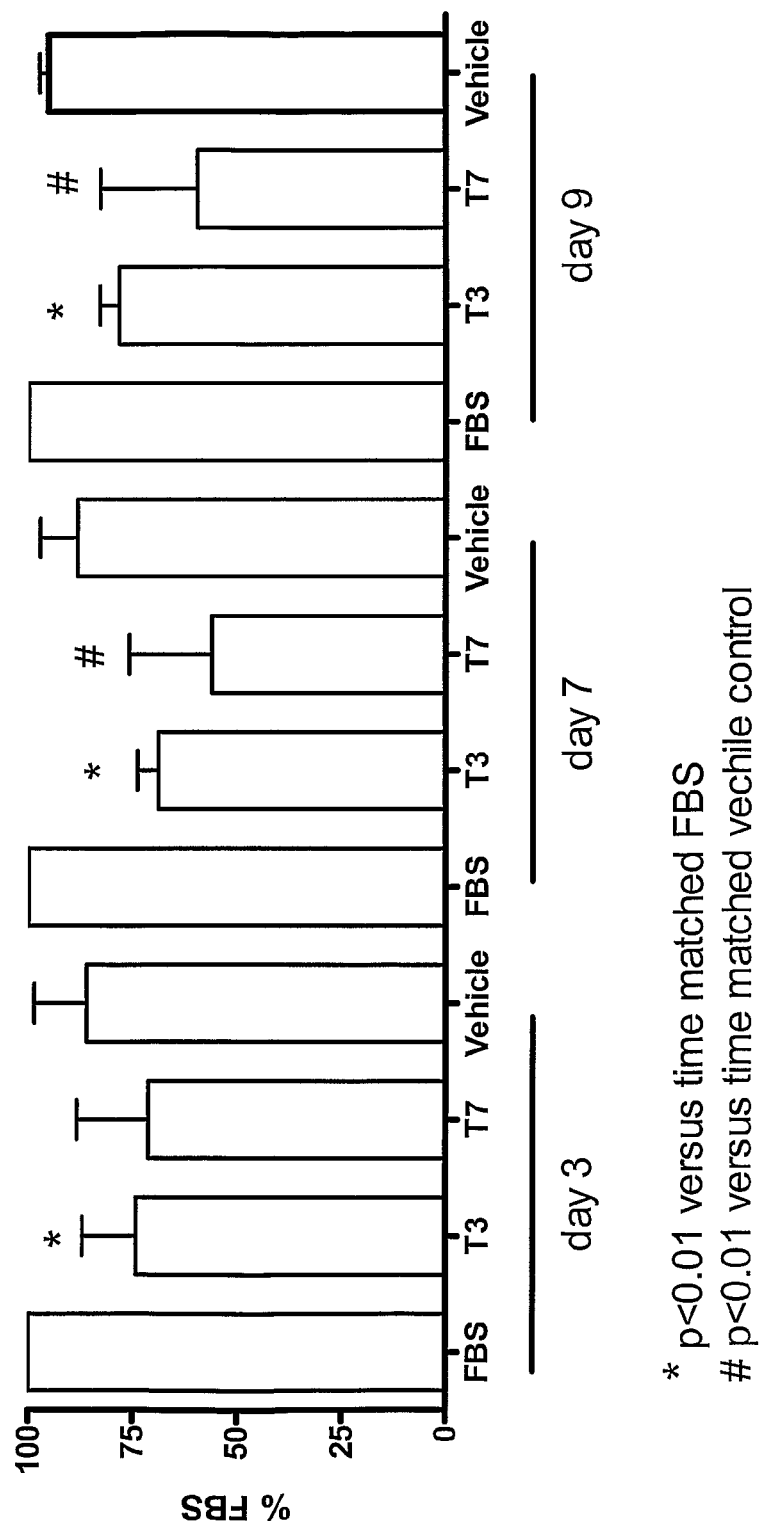
FIG. 12. The proliferation of primary lung endothelial cells was significantly inhibited by the presence of T3 peptide at all timepoints, whilst T7 peptide inhibited proliferation at both day 7 and day 9 in culture. Bars represent mean and the standard error of the mean. n=5 primary pulmonary endothelial cell lines derived from 5 independent volunteers.

Neither T3 nor T7 peptides were shown to be able to inhibit the proliferation of ASM cells from asthmatics (FIG. 11), non-asthmatics, or LAM sufferers, nor fibroblasts from non-asthmatics (Table 3). However as can be seen in FIG. 12, both T3 and T7 peptides were able to inhibit the proliferation of lung derived endothelial cells.

TABLE 3

The numbers in the table represent the percentage inhibition induced by the presence of T3, T7 or the T7 Vehicle control alone.

|  |  | Non-asthma ASM, n = 4 | LAM ASM, T3 n = 5 T7 n = 4 | COPD ASM, T3 n = 5 T7 n = 2 | NA Fibroblasts n = 2 |
|---|---|---|---|---|---|
| Day 3 | T3 | 13.4 | 0 | 0 | 0 |
|  | T7 | 7.4 | 0 | 9.7 | 5.0 |
|  | T7 vehicle control | 0 | 0 | 0 | 0 |
| Day 7 | T3 | 2.8 | 4.4 | 4.5 | ND |
|  | T7 | 1.2 | 0 | 0 | ND |
|  | T7 vehicle control | 0 | 0 | 0 | ND |
| Day 9 | T3 | 0 | 2.6 | 20.6 | 0 |
|  | T7 | 0 | 0 | 0 | 0 |
|  | T7 vehicle control | 2.7 | 0 | 0 | 0 |

Example 4

Tumstatin Inhibits Primary Lung Endothelial Cell Tube Formation

Endothelial cells are capable of differentiating to form blood vessels (capillaries). This process can be visualised in vitro using a tube formation assay. The ability of tumstatin to inhibit tube formation (angiogenesis) was assessed with the use of a specialised tube formation assay (BD BioCoat Angiogenesis system-endothelial cell tube formation, BD Biosciences, MA USA). Briefly, primary pulmonary endothelial cells isolated from 6 non-asthmatic individuals (isolated as described in Example 3) were seeded onto the 96 well plates at $4 \times 10^5$ cells/ml in F-12 (HAMS Nutrient F-12, JRH Biosciences) with endothelial cell growth supplement (ECG, BD Biosciences, MA USA) containing 10% FBS (GIBCO, Invitrogen corporation. Batch: 1236374). Tumstatin (Recombinant peptide, NC1 domain from bovine collagen IV, Weislab, Sweden) was added in duplicate wells at different concentrations (28 pg/ml, 84 pg/ml, 280 pg/ml, 840 pg/ml, and 2800 pg/ml); no tumstatin was added to duplicate wells to establish the baseline tube forming ability of each cell type tested. Following overnight incubation (37° C., 5% $CO_2$) tube formation (angiogenesis) was visualised using an inverted light microscope. Images were taken using a digital camera (Olympus CAMEDIA C-4000). At each concentration tested the total numbers of tubes within the well were counted from duplicate experiments per primary pulmonary endothelial cell line.

Figure 13:
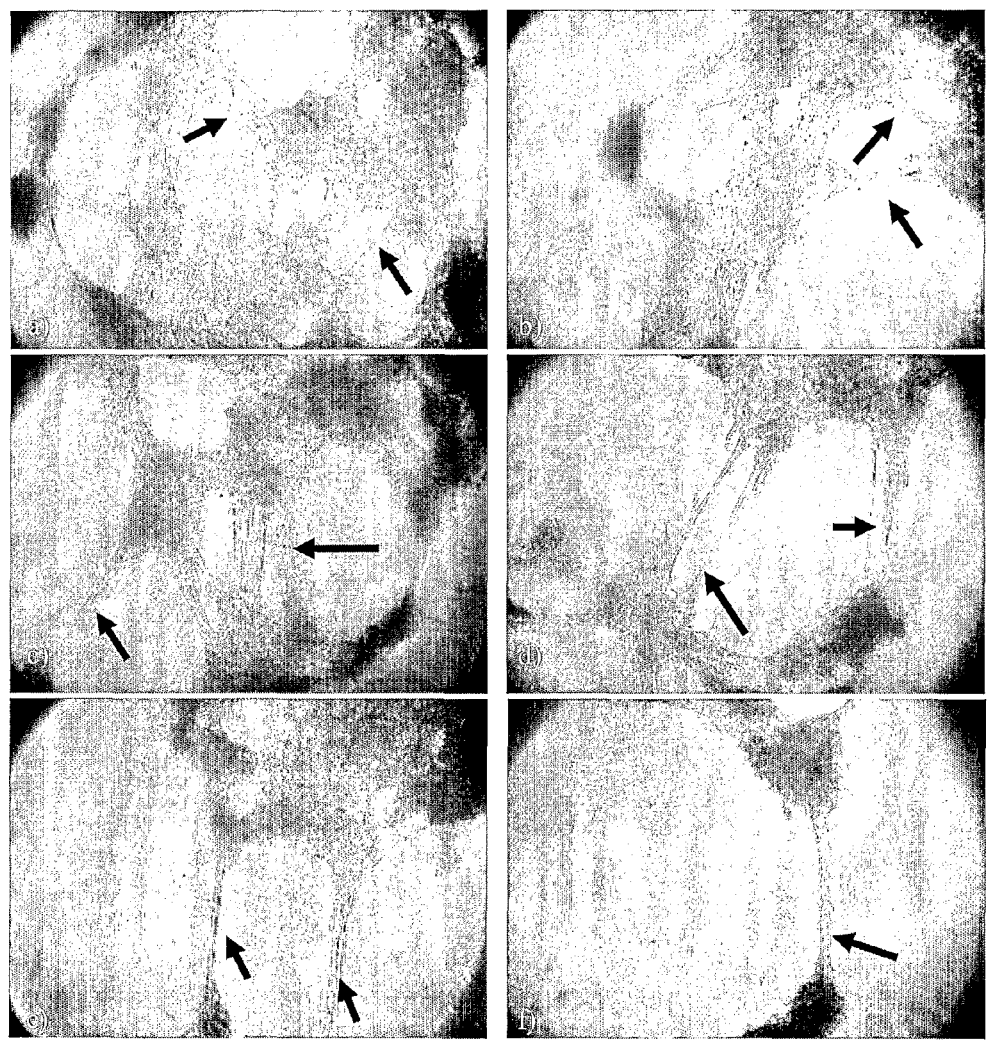
FIG. 13. A panel of images depicting visualisation of in-vitro angiogenesis of human primary pulmonary endothelial cells. Black arrows indicate the formation of tubes. In comparison to panel a) where no tumstatin was used, the number of tubes formed in panels b-f is reduced by the presence of tumstatin (28, 84, 280, 840 and 2800 pg/ml respectively). These images are derived from cells from a single volunteer and are representative of primary endothelial cells tested derived from six non-asthmatic volunteers.
Figure 14:
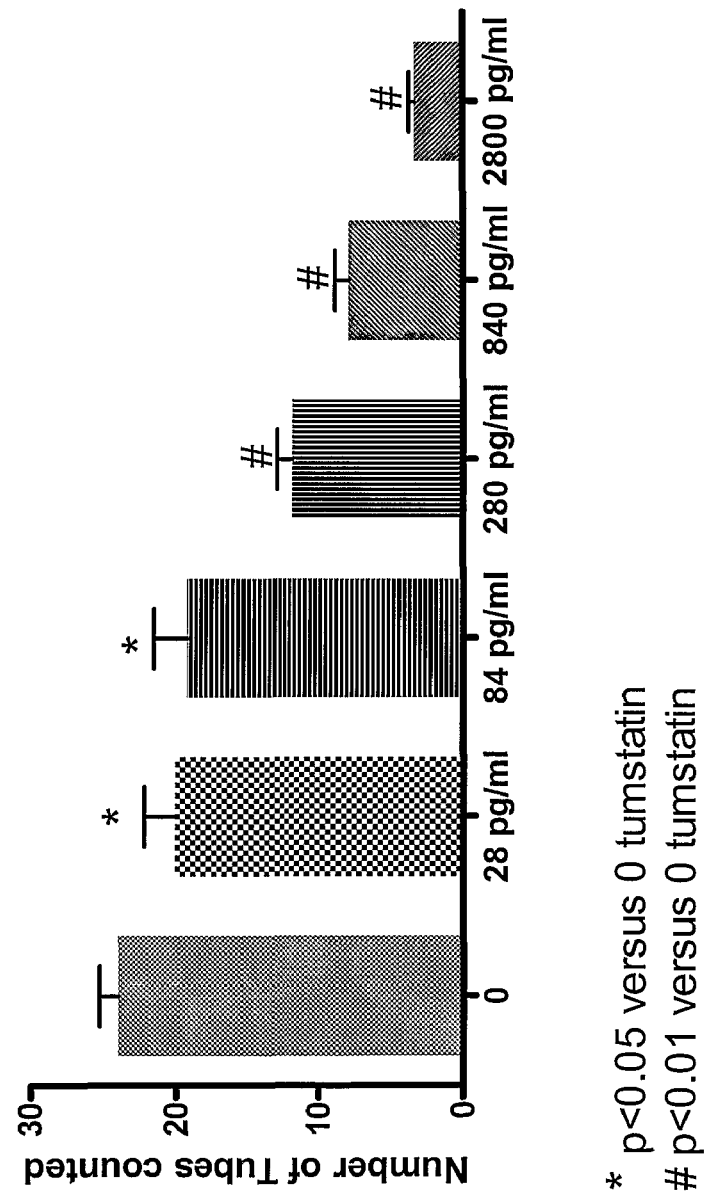
FIG. 14. The ability of tumstatin to inhibit the formation of tubes (blood vessels) by primary pulmonary endothelial cells was evaluated using an in-vitro angiogenesis assay. Tumstatin at the concentrations shown on the x axis inhibited the formation of tubes in primary pulmonary endothelial cells in a concentration related manner. At each concentration tested the total numbers of tubes within the well were counted from duplicate experiments per primary pulmonary endothelial cell line. Primary pulmonary endothelial cells were isolated and tested from six independent volunteers. Bars represent the mean +/− standard error of the mean. Data were statistically analysed using repeated measures one way ANOVA with Dunnett's post test.

For the first time, the inventors have demonstrated that primary pulmonary endothelial cells are able to form tubes and importantly tube formation was reduced in a concentration related manner by the addition of tumstatin. Tumstatin at concentrations of 28 and 84 pg/ml resulted in a small, but statistically significant, reduction in the formation of tubes ($p<0.05$, n=6, repeated measures one way ANOVA with Dunnett's post test). However at a concentration of 280 pg/ml approximately 40% of the tube formation was inhibited. This inhibition was further increased to 60% and 75% when cells were treated with 840 and 2800 pg/ml respectively. Photomicrographs from a single endothelial cell line are shown in FIG. 13, and the combined data from all six endothelial cell lines tested are shown graphically in FIG. 14.

Example 5

Tumstatin Inhibits Lung Angiogenesis and the Development of Airway Hyperresponsiveness in Murine Models of Asthma To ensure that tumstatin would be an effective treatment for asthma the inventors investigated whether tumstatin could inhibit the development of pulmonary angiogenesis and airway hyperresponsiveness (asthma) in two different murine models of asthma. The first model used was a virus (mouse pneumonia virus, PVM) induced model of asthma, and the second model was a classical ovalbumin-induced asthma model which is known to induce anigiogenesis (Lee et al., 2006)

(i) PVM Asthma Model

Newborn Balb/c mice (<24 hrs old) were infected intranasally (IN) with a low dose (2.5 plaque forming units) of PVM strain J3666 in 5 ul in DMEM containing 10% FCS. To investigate whether angiogenesis was occurring in response to PVM infection the mice were sacrificed at 7, 14, 21, 28, 35, 49 and 96 days post infection, and the left lung removed, and fixed in 4% formaldehyde solution prior to use in immunohistochemical analysis. We also treated some mice concurrently IN with tumstatin and PVM. Briefly, newborn mice were infected with low dose PVM as before and tumstatin reconstituted in PBS was given to the mice IN at 300 ng per 20 g body weight. Tumstatin was administered for the first 10 days, and then at days 21, 24 and 27 post infection. As per ethical guidelines, mice were lightly anaesthetised once they were 10 days old with isofluorane prior to the administration of tumstatin.

(ii) OVA Asthma Model

A chronic asthma model was generated as follows. Adult Balb/c mice (6-8 weeks old) were administered ovalbumin (OVA) on days 0, 7, 14 and 21: (25 µg OVA and 1 mg aluminium hydroxide in 200 µl sterile PBS subcutaneously [SC]). On days 26, 29 and 31, 20 ng OVA in 50 µl sterile PBS was administered intranasally (IN), and then twice weekly from days 32-115. Some of the mice in the chronic asthma model were administered tumstatin (reconstituted in PBS) IN at either 600 ng or 300 ng per 20 g body weight once a day from days 25-115. Sham treatment was as follows: Adult Balb/c mice (6-8 weeks old) were administered 1 mg aluminium hydroxide in 200 µl sterile PBS SC on days 0, 7, 14 and 21. On days 26, 29 and 31, 50 µl sterile PBS was administered IN. 20 ng OVA in 50 µl sterile PBS was administered 1N, twice weekly from days 32-115. The airway resistance to inhaled methacholine was calculated on day 115, at this time point the animals were sacrificed and the left lung removed and fixed in 4% formaldehyde solution prior to use in immunohistochemical analysis.

Determination of airway hyperresponsiveness (AHR) was measured to increasing concentrations of inhaled methacholine in vivo by measuring changes in transpulmonary resistance ($R_L$) and dynamic compliance ($C_{dyn}$) using a supine whole-body plethysmograph (Buxco Electronics Inc) attached to a computer. Mice were anaesthetised with an intraperitoneal injection of ketamine/xylazine and cannulated via the trachea with an 18G metal tube. Mice were mechanically ventilated by a Minivent mouse ventilator at a rate of 120 breaths per minute and a tidal volume of 8 ml/kg. Changes in ling volume were detected by a differential transducer connected to the plethysmograph chamber lumen which measured volume changes due to thoracic expansion with ventilation. A pressure transducer with a port near the tracheal tube measured alterations in tracheal pressure as a function of airway calibre. Aerosolised acetyl-β-methacholine (1.25, 2.5, 5, and 10 mg/mil) in PBS generated by an ultrasonic nebuliser was delivered directly to the lungs via the inspiratory line for 5 minutes. The peak response to methacholine was compared to the response to saline alone.

Figure 15:
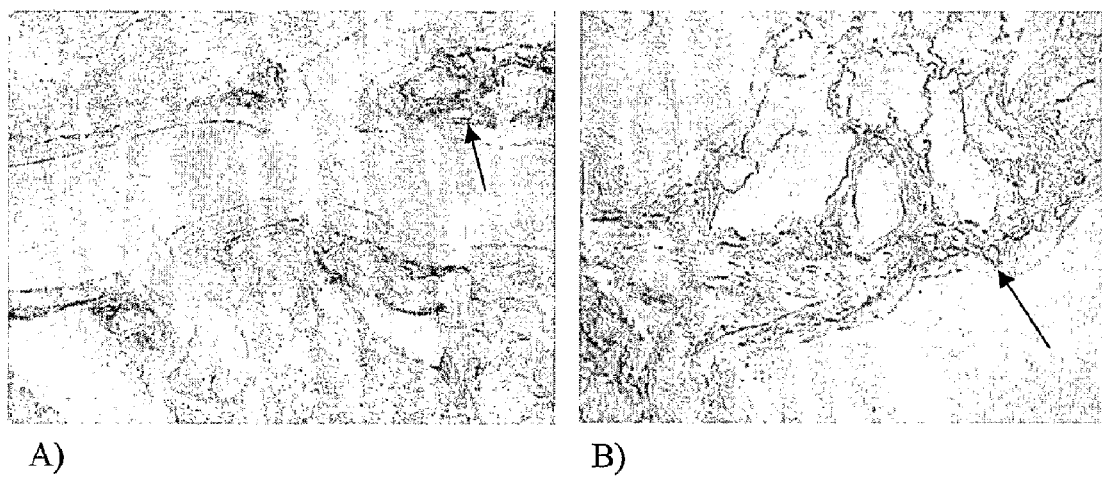
FIG. 15. A) Images depicting positive staining (indicated by the arrow) for vWF in sections from a murine lung, however the staining is not associated with a tubular (blood vessel) structure and would therefore be classified as non-specific. However, as demonstrated in B) positive staining (indicated by the arrow) for vWF in sections from a murine lung is associated with a tubular (blood vessel) structure and would therefore be classified as a blood vessel.

For immunohistochemical examination of tissue, paraffin embedded lung tissue sections were placed in xylene for 30 mins, for de-paraffinisation, and re-hydrated through graded alcohol. Sections were blocked with a pre-made peroxidase blocking agent (DakoCytomation, CA USA) for 5 minutes. Sections were then washed with PBS and primary antibodies were added, goat anti-mouse CD31 (PECAM-1) (Santa Cruz Biotechnology Inc, CA USA) at 1:100 dilution and rabbit anti-mouse Von Willebrand factor (vWF) (Santa Cruz Biotechnology Inc, CA USA) at 1:100 dilution, and incubated at room temperature for one hour. Both CD31 and vWF are blood vessel markers. Sections were washed in PBS and the secondary antibodies were added, pre-made anti-rabbit Horseradish peroxidase (HRP) (DakoCytomation, CA USA) and rabbit anti-goat HRP (DakoCytomation, CA USA) respectively, and incubated at room temperature for one hour. Sections were washed in PBS for 5 minutes and a pre-made substrate chromogen, liquid DAB (DakoCytomation, CA USA), was added to the sections and incubated for 5 minutes at room temperature. Sections were then washed in distilled water for 5 minutes and mounted using an aqueous mounting medium (Faramount, DakoCytomation, CA USA) and coverslipped. Images were taken on an Olympus fluorescence microscope and captured using Leica imaging software. Blood vessels were discriminated from surrounding tissue by the presence of a tubular structure and the presence of positive staining for either vWF or CD31 (FIG. 15).

Tumstatin Administration in the PVM Model

Figure 16:
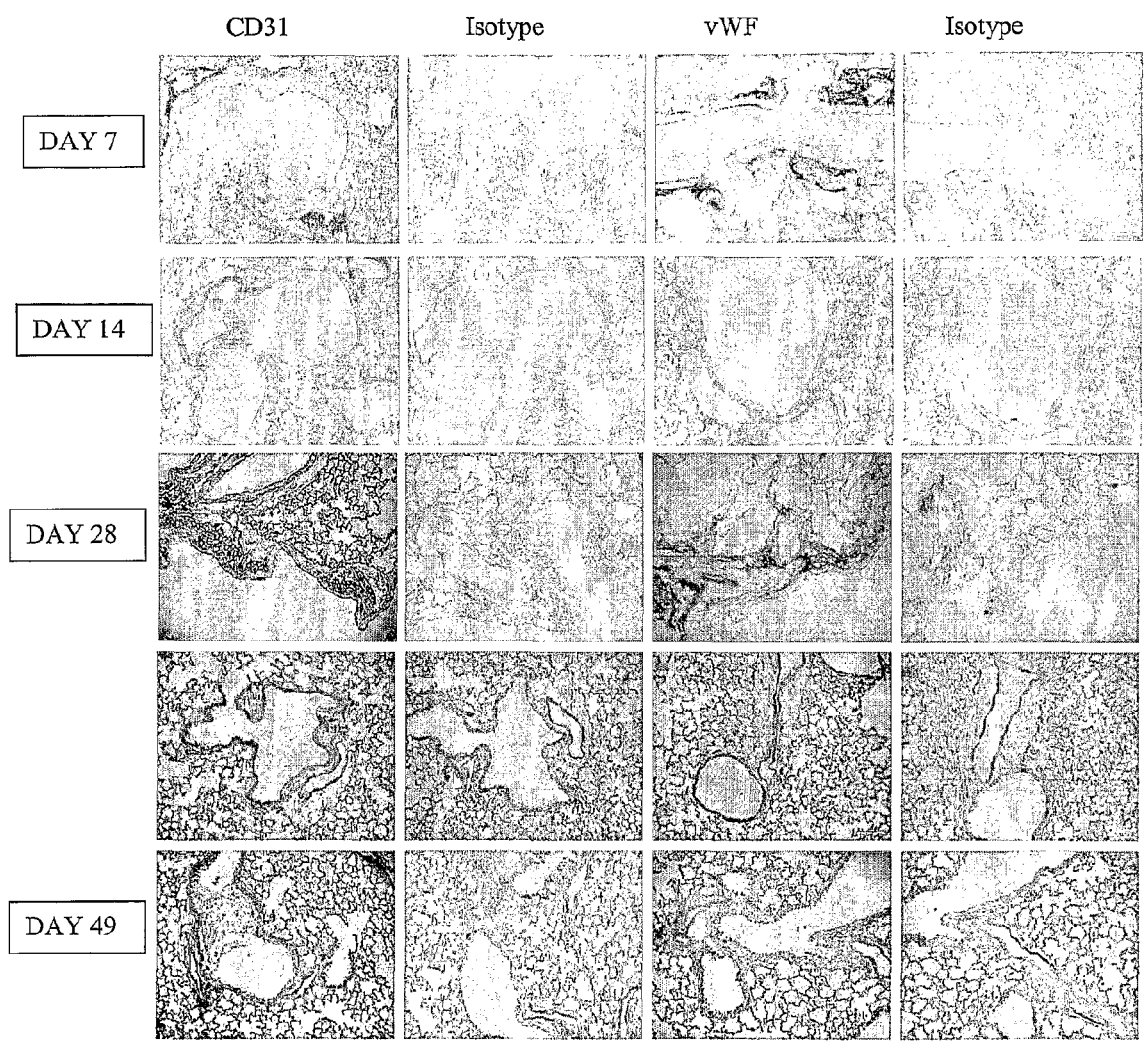
FIG. 16. Images depicting staining for the blood vessel markers CD31 and vWF and the appropriate isotype controls, in mice which had previously been infected with PVM. There is a clear increase in the number of blood vessels which stain positively at day 28 with both markers, which subsequently decreases at latter timepoints. These immunohistochemical images are derived from 5 different mice (one mouse per timepoint) and are representative of all six mice tested at each time point.

Lungs of the mice (six per timepoint) which received treatment with PVM alone were assessed for the presence of angiogenesis. As shown in FIG. 16, where brown staining indicates immunoreactivity (i.e. specific antibody binding) there was a clear increase in blood vessel number at day 28, which subsequently decreased at the latter time points. Four independent observers counted the number of blood vessels in four random fields from each of the six mice at days 14, 28 and 35, in comparison to images of the appropriate isotype controls, for each factor (CD31 or vWF) investigated. The mean number of blood vessels per image (combined CD31 and vWF) at day 14 was $0.63^{+}/-0.31$ (SEM), which dramatically increased at day 28 to $35.6^{+}/-3$, and subsequently reduced to $0.34^{+}/-0.34$ by day 35.

Figure 17:
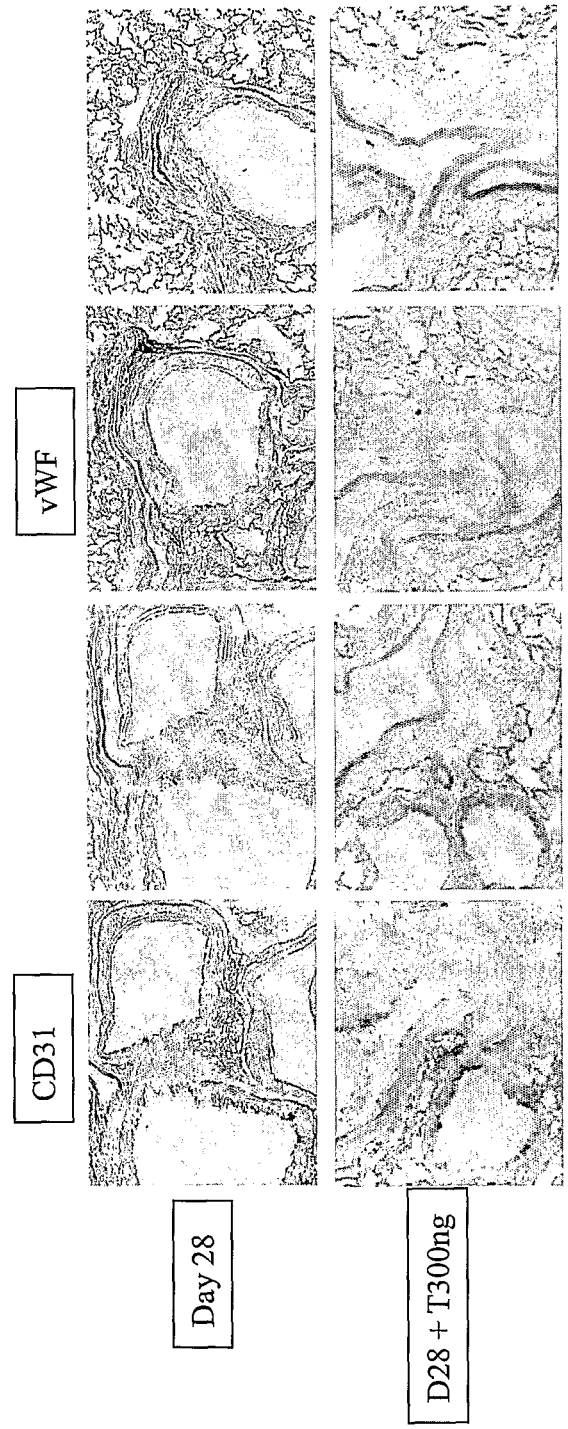
FIG. 17. Images depicting staining for the blood vessel markers CD31 and vWF and the appropriate isotype controls. In comparison to the mice which had been infected with PVM alone (top panel), prior concurrent administration of tumstatin to PVM infected mice clearly reduced the number of positively stained blood vessels. These immunohistochemical images are derived from 2 different mice (one mouse per timepoint) and are representative of all six mice which had PVM infection alone, and the 4 mice which received tumstatin treatment during PVM infection.

As it had been shown that angiogenesis was occurring by day 28, it was investigated whether treatment with tumstatin could inhibit the development of pulmonary angiogenesis. As shown in FIG. 17, treatment with tumstatin at 300 ng per 20 g body weight inhibited the development of angiogenesis.

Tumstatin, administration in the OVA Model

Figure 18:
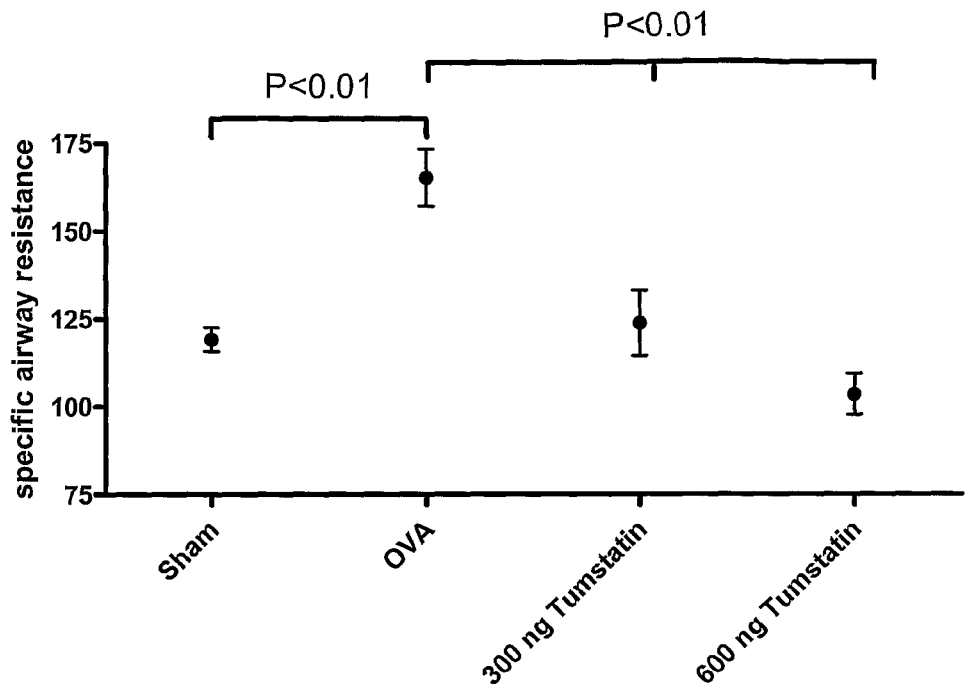
FIG. 18. Graphical representation of the airway hyperresponsiveness induced by inhalation of methacholine (10 mg/ml). A) Mice which were sensitised and subsequently chronically exposed to OVA had increased airway resistance in comparison to sham treated animals ($p<0.01$, $n=4$, two way ANOVA with Bonferroni posttests). However concurrent administration of tumstatin and OVA significantly reduced airway hyperresponsiveness in comparison to the OVA sensitised and exposed group at both concentrations of tumstatin used (for both, $p<0.01$, $n=4$, two way ANOVA with Bonferroni posttests) B) Mice which were sensitised and subsequently chronically exposed to OVA had decreased airway conductance in comparison to sham treated animals ($p<0.05$, $n=4$, two way ANOVA with Bonferroni posttests). However concurrent administration of tumstatin and OVA significantly increased airway conductance in comparison to the OVA sensitised and exposed group only in the 600 ng tumstatin group ($p<0.05$, $n=4$, two way ANOVA with Bonferroni posttests).
Figure 18:
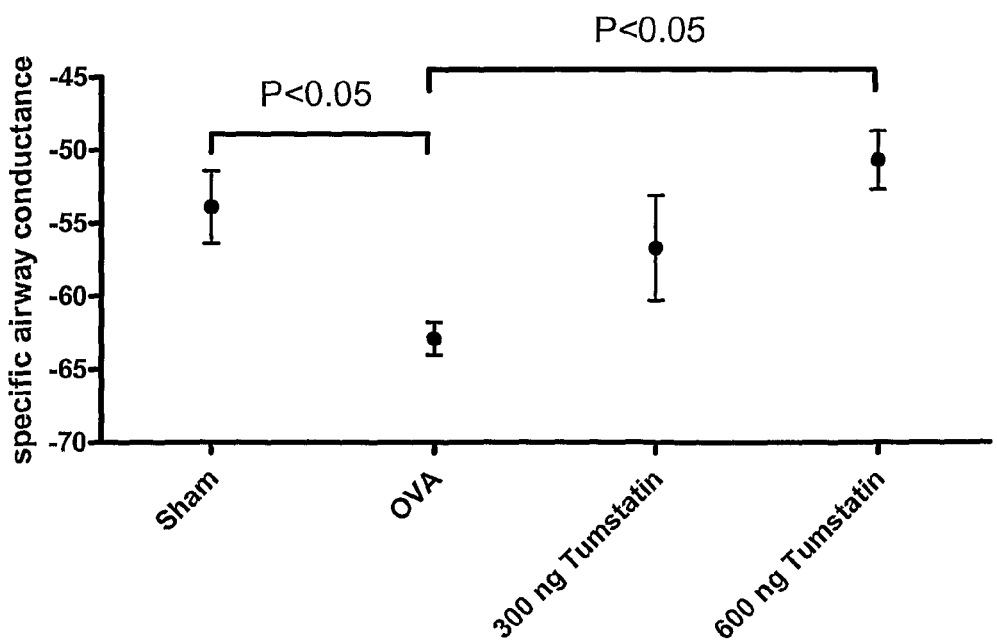

The mice which received treatment with OVA alone demonstrated an increase in specific airway resistance to methacholine (10 mg/ml) in comparison to sham (naive) treated animals demonstrating that a murine model of asthma had been successfully established ($p<0.01$, n=4, one way ANOVA with Dunnett's Multiple Comparison Test; see FIG. 18A).

The mice which had received concurrent treatment with tumstatin at 300 ng per 20 g body weight and OVA had reduced specific airway resistance to methacholine (10 mg/ml) in comparison to OVA alone $p<0.01$, n=4, two way ANOVA with Bonferroni posttests; FIG. 18A) which was similar to that observed in the sham treated animals. Moreover, the mice which had received concurrent treatment with tumstatin at 600 ng per 20 g body weight and OVA also had reduced specific airway resistance to methacholine (10 mg/ml) in comparison to OVA alone ($p<0.01$, n=4, two way ANOVA with Bonferroni posttests; FIG. 18A) and was reduced below the level observed in the sham treated animals. Similarly, mice which were sensitised and subsequently chronically exposed to OVA had decreased airway conductance in comparison to sham treated animals ($p<0.05$, n=4, two way ANOVA with Bonferroni posttests; FIG. 18B). Concurrent administration of tumstatin at 600 ng per 20 g body weight and OVA significantly increased airway conductance in comparison to the OVA sensitised and exposed group ($p<0.05$, n=4, two way ANOVA with Bonferroni posttests; FIG. 18B).

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations of any two or more of said steps or features.

References

Bunin et al. (1994) *Proc. Natl. Acad. Sci. USA*, 91:4708-4712.
DeWitt et al. (1993) *Proc. Natl. Acad. Sci. USA*, 90:6909-6913
Erlich, 1989, eds, *PCR Technology*, Stockton Press, NY
Fodor et al (1991) *Science* 251(4995):767-73
Goeddel et al., 1980, *Nucleic Acids Res.* 8:4057
Johnson et al., 1995 *Am J Physiol* 269:L514-519.
Kazal et al., 1996, *Nature Medicine* 2: 753-759
Lawn et al., 1981, *Nucleic Acids Res.* 2: 6103
Lee et al. 2006, *J Allergy Clin Immunol*, 117:597-603.
Maeshima, et al. 2000, *J Biol Chem*, 275:23745-23750.
Maeshima, et al. 2001, *J Biol Chem*, 276:31959-31968.
Moore et al 1988, *BBA*, 1402:239-249
Mullis et al., 1987, *Quant. Biol.* 51:263
Stein and Cohen, 1988, *Cancer Res* 48:2659-68
Sudhakar et al, 2003, *Nat. Acad. Sci.* 100:4766-4771
van der Krol et al., 1988, *Biotechniques* 6:958-976
Wedemeyer et al 2002, *Clinical Chemistry* 48:9 1398-1405
Weissleder et al 2000, *Nature Medicine*, 6:351-355

What is claimed is:

1. A method for improving airway conductance in a subject with a condition associated with airway remodeling, the method comprising administering to the subject an effective amount of an NC1 domain of an α3 chain of type IV collagen or a functionally active fragment thereof that inhibits proliferation of endothelial cells.

2. The method of claim 1 wherein the condition is selected from asthma, lymphangioleiomyomatosis (LAM), pulmonary fibrosis and cystic fibrosis.

3. The method of claim 1, wherein a fragment of an NC1 domain of the α3 chain of type IV collagen comprising the amino acid sequence set forth in SEQ ID NO: 8 is administered.

4. The method of claim 3, wherein the fragment comprises the amino acid sequence set forth in SEQ ID NO: 6 or SEQ ID NO: 7.

5. The method of claim 1, wherein the NC1 domain of an α3 chain of type IV collagen is from human type IV collagen.

6. A method for the treatment of a condition characterized by aberrant or otherwise unwanted airway tissue remodeling in a subject, said method comprising administering to the subject an effective amount of the NC1 domain of the α3 chain of type IV collagen or a functionally active fragment thereof that inhibits proliferation of endothelial cells.

7. The method of claim 6 wherein the condition is selected from asthma, lymphangioleiomyomatosis (LAM), pulmonary fibrosis and cystic fibrosis.

8. The method of claim 7 wherein the condition is asthma.

9. The method of claim 7 wherein the condition is LAM.

10. The method of claim 6 wherein the airway tissue is tracheal, bronchus or bronchiolar tissue.

11. The method of claim 6 wherein the condition is LAM and the method further comprises administering to the subject an effective amount of the NC1 domain of the α5 chain of the type IV collagen.

12. The method of claim 6, wherein a fragment of an NC1 domain of the α3 chain of type IV collagen comprising the amino acid sequence set forth in SEQ ID NO: 8 is administered.

13. The method of claim 12, wherein the fragment comprises the amino acid sequence set forth in SEQ ID NO: 6 or SEQ ID NO: 7.

* * * * *